United States Patent
Miyauchi et al.

(10) Patent No.: US 11,019,995 B2
(45) Date of Patent: Jun. 1, 2021

(54) RETINAL SCANNING TYPE EYE EXAMINATION DEVICE, RETINAL SCANNING TYPE EYE EXAMINATION SYSTEM, EYEWEAR PROVISION SYSTEM, AND RETINAL SCANNING TYPE EYEWEAR

(71) Applicant: QD Laser, Inc., Kanagawa (JP)

(72) Inventors: Hironori Miyauchi, Kanagawa (JP); Kenji Yasui, Kanagawa (JP); Mitsuru Sugawara, Kanagawa (JP); Makoto Suzuki, Kanagawa (JP)

(73) Assignee: QD Laser, Inc., Kanagawa (JP)

( * ) Notice: Subject to any disclaimer, the term of this patent is extended or adjusted under 35 U.S.C. 154(b) by 238 days.

(21) Appl. No.: 16/471,274

(22) PCT Filed: Dec. 19, 2017

(86) PCT No.: PCT/JP2017/045581
§ 371 (c)(1),
(2) Date: Jun. 19, 2019

(87) PCT Pub. No.: WO2018/123741
PCT Pub. Date: Jul. 5, 2018

(65) Prior Publication Data
US 2020/0085295 A1 Mar. 19, 2020

(30) Foreign Application Priority Data
Dec. 27, 2016 (JP) .............................. JP2016-253984

(51) Int. Cl.
*A61B 3/11* (2006.01)
*A61B 3/10* (2006.01)
*A61B 3/16* (2006.01)

(52) U.S. Cl.
CPC ............ *A61B 3/111* (2013.01); *A61B 3/1025* (2013.01); *A61B 3/165* (2013.01); *A61B 2562/028* (2013.01)

(58) Field of Classification Search
CPC ....... A61B 3/111; A61B 3/1025; A61B 3/165; A61B 2562/028; A61B 3/0033; A61B 3/12; G02C 11/10; G02C 13/005
(Continued)

(56) References Cited

U.S. PATENT DOCUMENTS 8,223,024 B1 7/2012 Petrou
2009/0201467 A1* 8/2009 Smith ...................... A61B 3/14
351/206
(Continued)

FOREIGN PATENT DOCUMENTS

EP 0562742 9/1993
JP 2002-162607 6/2002
(Continued)

OTHER PUBLICATIONS

Partial European search report for European Patent Application No. 17887628.0 dated Nov. 28, 2019.
(Continued)

*Primary Examiner* — Mohammed A Hasan
(74) *Attorney, Agent, or Firm* — IPUSA, PLLC

(57) ABSTRACT

A retinal scanning type eye examination device includes a storage unit configured to store test image data; a laser emitting unit including a laser light source configured to generate an imaging laser beam based on the test image data, the laser emitting unit being configured to project a test image onto a retina of an eyeball of a person subjected to an eye examination by using the imaging laser beam; an optical component configured to cause the imaging laser beam to converge at an inside of the eyeball of the person; a parameter acquiring unit configured to acquire parameter information for a retinal scanning type eyewear, the parameter information including angle information indicating a rotation angle of the laser emitting unit when the laser emitting unit is rotated around a converging point of the laser beam; and an output unit configured to output the parameter information to an external device.

13 Claims, 20 Drawing Sheets

(58) Field of Classification Search
USPC .......................................................... 351/206
See application file for complete search history.

(56) References Cited

U.S. PATENT DOCUMENTS

| | | |
|---|---|---|
| 2012/0002167 A1 | 1/2012 | Kondoh |
| 2012/0069302 A1 | 3/2012 | Juhasz et al. |
| 2014/0333898 A1 | 11/2014 | Boate et al. |

FOREIGN PATENT DOCUMENTS

| | | |
|---|---|---|
| JP | 2007-130495 | 5/2007 |
| JP | 2012-011146 | 1/2012 |
| JP | 2013-537092 | 9/2013 |
| WO | 2013049248 | 4/2013 |

OTHER PUBLICATIONS

Extended European search report for European Patent Application No. 17887628.0 dated Mar. 9, 2020.
Eiji Shimizu, "Retinal Scanning/Projection Display", The Journal of the Institute of Image Information and Television Engineers, 2011, vol. 65, No. 6, pp. 758-763, with partial English translation.
International Search Report for PCT/JP2017/045581 dated Jan. 23, 2018.

* cited by examiner

FIG.5
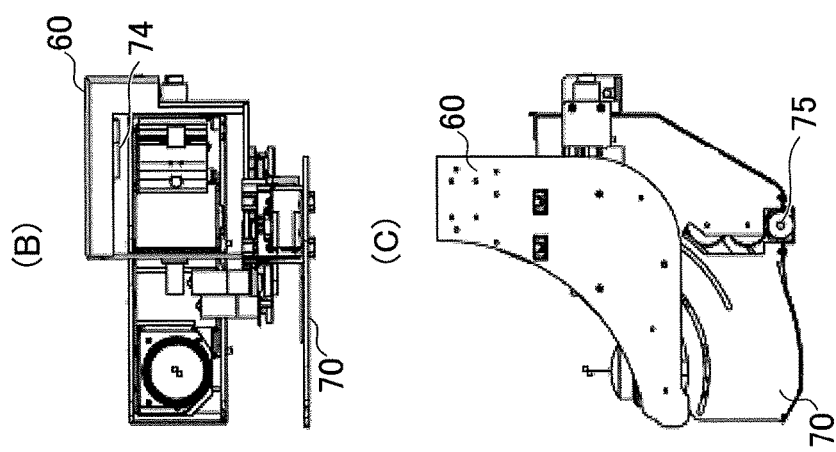
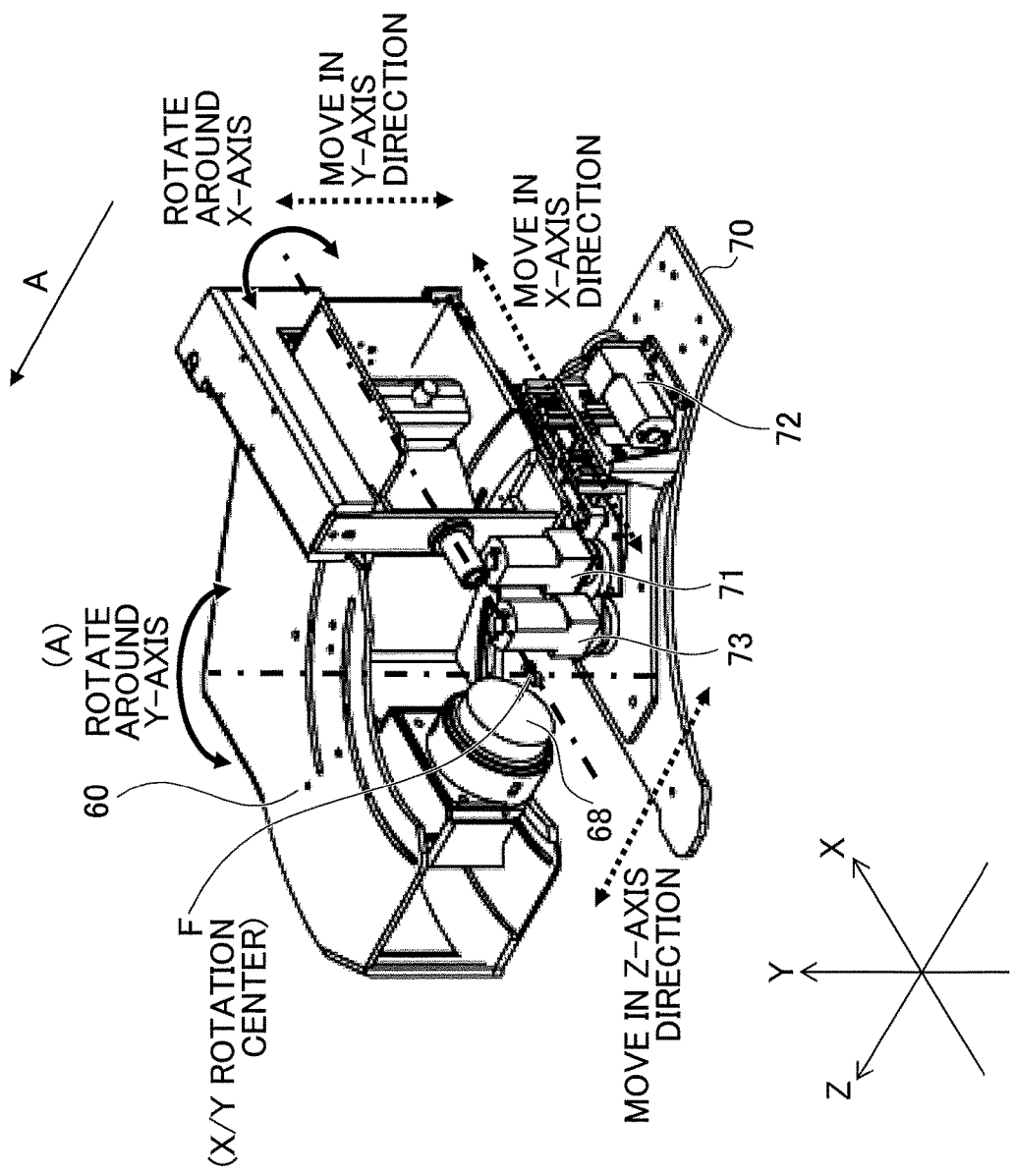

FIG.16
(A)
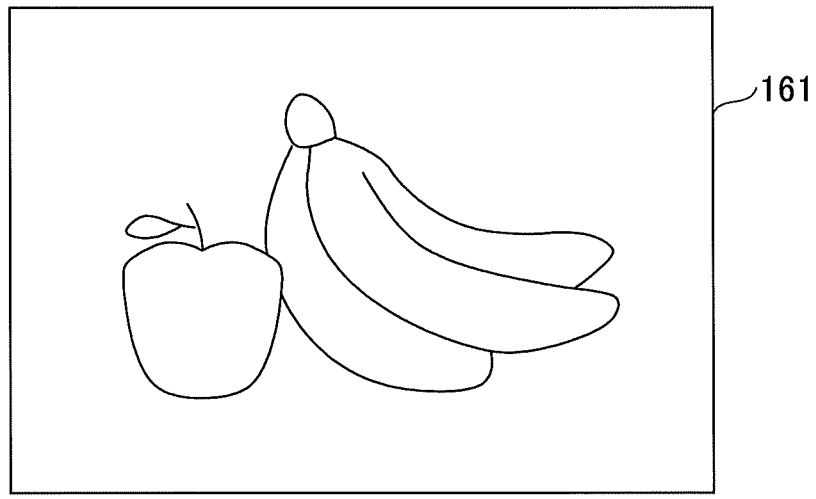
(B)
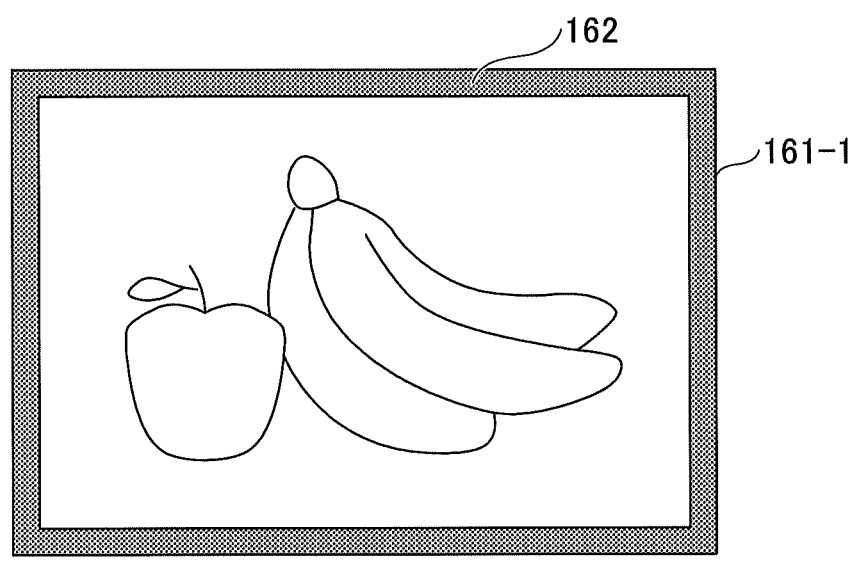

FIG.22A
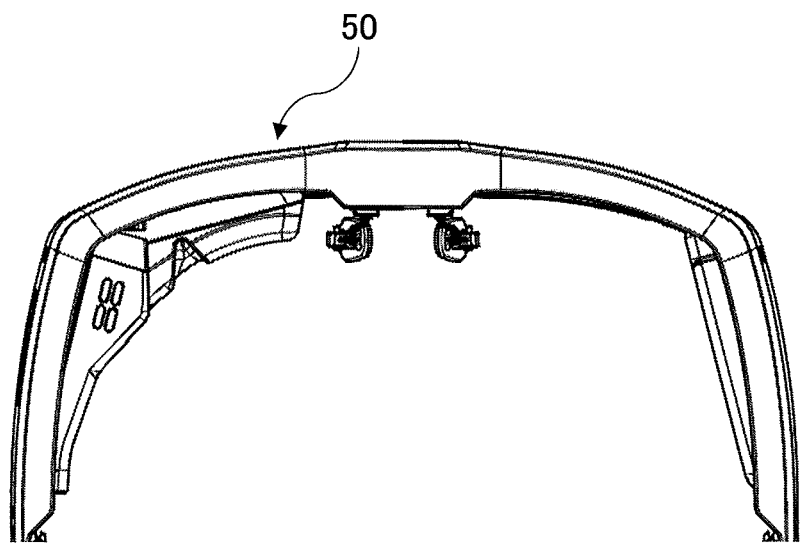
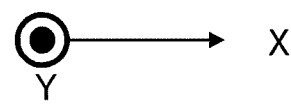
FIG.22B
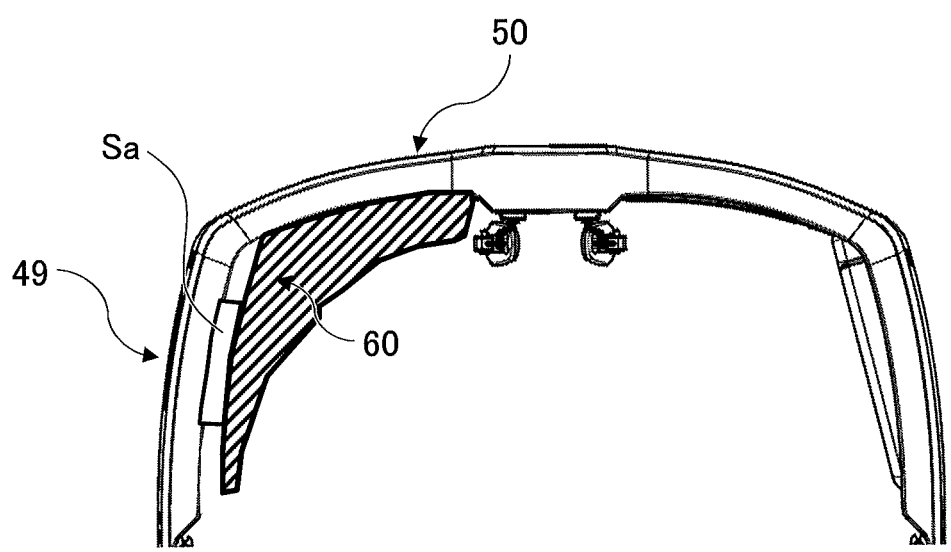
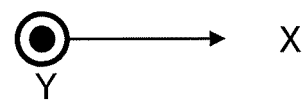

RETINAL SCANNING TYPE EYE EXAMINATION DEVICE, RETINAL SCANNING TYPE EYE EXAMINATION SYSTEM, EYEWEAR PROVISION SYSTEM, AND RETINAL SCANNING TYPE EYEWEAR

TECHNICAL FIELD

The present invention relates to a retinal scanning type eye examination device, a retinal scanning type eye examination system, a retinal scanning type eye examination method, a retinal scanning type eyewear provision system, a retinal scanning type eyewear provision method, and a retinal scanning type eyewear.

BACKGROUND

Background Art

Traditionally, various types of eye examinations are conducted using an eye examination instrument or an ophthalmoscopic device. In the eye examination, a method of displaying a test image and of letting an examinee to recognize the test image has been known (Patent Document 1). In addition, it has been known that a seller of eyeglasses and the like acquires data required to make a lens or frame of the eyeglasses for each user, and the seller sends this data to a processing factory of the eyeglasses (Patent Document 2).

Recently, a retinal scanning type head-mounted display utilizing Maxwellian view has been known. Maxwellian view is a method for causing a person to visually recognize an image represented by image data to a person without being affected by an accommodative function of a lens of the user's eye by projecting a light beam based on the image data on a retina after the light beam is converged once at the center of a pupil.

When manufacturing the retinal scanning type head-mounted display, various user-specific parameters are required depending on a state of a user's eye. Accordingly, when a retinal scanning type head-mounted display is manufactured and sold, the following procedures are required, for example. First, a retinal scanning type head-mounted display is placed on a user to acquire user parameters. Next, a customizing operation is performed based on the acquired user parameters.

CITATION LIST

Patent Document

[Patent Document 1] Japanese Laid-open Patent Application Publication No. 2002-130495
[Patent Document 2] Japanese Laid-open Patent Application Publication No. 2002-162607

SUMMARY

Problem to be Solved by the Invention

Because the above-described procedures for the method of manufacturing and selling the retinal scanning type head-mounted display are complex, an improvement of efficiency is desired.

However, in the above-described method of selling eyeglasses, only data on lenses and frames can be acquired, and parameters necessary for projecting an image onto a user's retina cannot be acquired. Further, in the conventional eye examination technique, if an examinee has a disease in the anterior portion of his/her eye, an eye examination including his/her retina cannot be made.

The disclosed technology is developed in light of the above-mentioned circumstances, and is intended to improve manufacturing efficiency of a retinal scanning type head-mounted display.

Means for Solving Problem

The disclosed technology is a retinal scanning type eye examination device including a storage unit configured to store test image data; a laser emitting unit including a laser light source configured to generate an imaging laser beam based on the test image data, the laser emitting unit being configured to project a test image onto a retina of an eyeball of a person subjected to an eye examination by using the imaging laser beam; an optical component configured to cause the imaging laser beam to converge at an inside of the eyeball of the person; a parameter acquiring unit configured to acquire parameter information for a retinal scanning type eyewear, the parameter information including angle information indicating a rotation angle of the laser emitting unit when the laser emitting unit is rotated around a converging point of the laser beam; and an output unit configured to output the parameter information to an external device.

Effect of Invention

Efficiency of production of a retinal scanning type head-mounted display is improved.

BRIEF DESCRIPTION OF THE DRAWINGS

FIG. 5 is a diagram illustrating a configuration of an eyepiece device;

FIG. 16 is a diagram illustrating image processing according to the second embodiment;

FIG. 22A illustrates an eyewear prior to application of a pupil-to-pupil distance; and FIG. 22B illustrates an eyewear after application of the pupil-to-pupil distance.

DESCRIPTION OF EMBODIMENTS

First Embodiment

Figure 1:
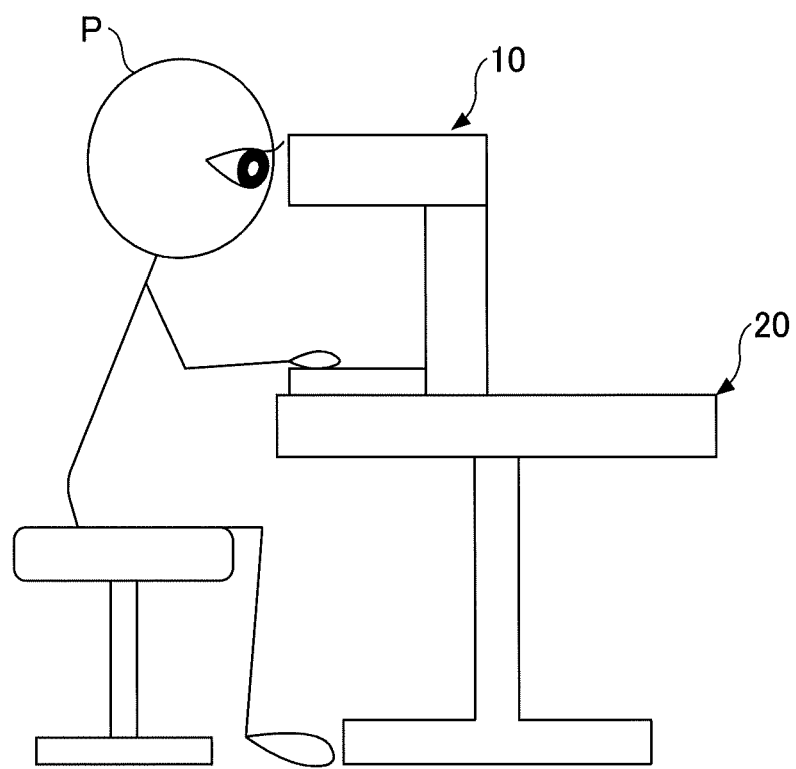
FIG. 1 is a diagram illustrating an eye examination device according to a first embodiment.

Hereinafter, a first embodiment will be described with reference to the drawings. FIG. 1 is a diagram illustrating an eye examination device according to a first embodiment.

The eye examination device 10 of the present embodiment is a retinal scanning type eye examination device. Specifically, the eye examination device 10 according to the present embodiment retains image data for examination (test image data), and by irradiating a retina of a person P subjected to an eye examination (examinee P or subject P) with a laser beam based on the test image data, an image for examination (test image) is projected onto the retina of the subject P. Next, the eye examination device 10 receives, from the subject P, an input of, for example, an operation to adjust a position of a laser emitting unit of the eye examination device 10, information indicating a method of viewing the test image, and the like.

Based on the input information, the eye examination device 10 generates and outputs parameter information for projecting an image on the retina of the subject P. In addition, the eye examination device 10 according to the present embodiment may generate eye examination result information of the eye of the subject P based on the input information, and retain or output the test result information.

The parameter information of the subject P is information that includes, for example, a pupil-to-pupil distance of the subject P, a visual field of the subject P, a distance from the laser emitting unit to the focal point of the subject P, the angle of the laser beam emitted from a laser light source, and the like. In other words, the parameter information of the present embodiment is information indicating a region scanned by the laser beam in the retina of the subject P. Further, the eye examination result information is information indicating a result of an eye examination of the subject P, which is, in other words, information indicating a status of the eyeball of the test subject P. Details of the parameter information and the eye examination result information will be described below.

The eye examination device 10 according to the present embodiment is mounted on a pedestal 20 or the like, and an eye examination is performed with the eyes brought close to an eyepiece device of the eye examination device 10 such that the subject P is looking inside the eyepiece device. The example of FIG. 1 illustrates a case in which an eye examination is conducted while the subject P is sitting on a chair, but a mode of an eye examination is not limited to the case illustrated in FIG. 1. The subject P may conduct the eye examination while he/she is standing.

The eye examination device 10 according to the present embodiment may be installed, for example, in a store where a retinal scanning type head-mounted display (hereinafter referred to as an eyewear) is sold, or in a hospital (ophthalmological clinic, etc.). Also, the eye examination device 10 according to the present embodiment may be installed in a gymnasium, a sports gym, a commercial facility, or the like. The eye examination device 10 according to the present embodiment may be installed at any location as long as the subject P can conduct an eye examination.

Figure 2:
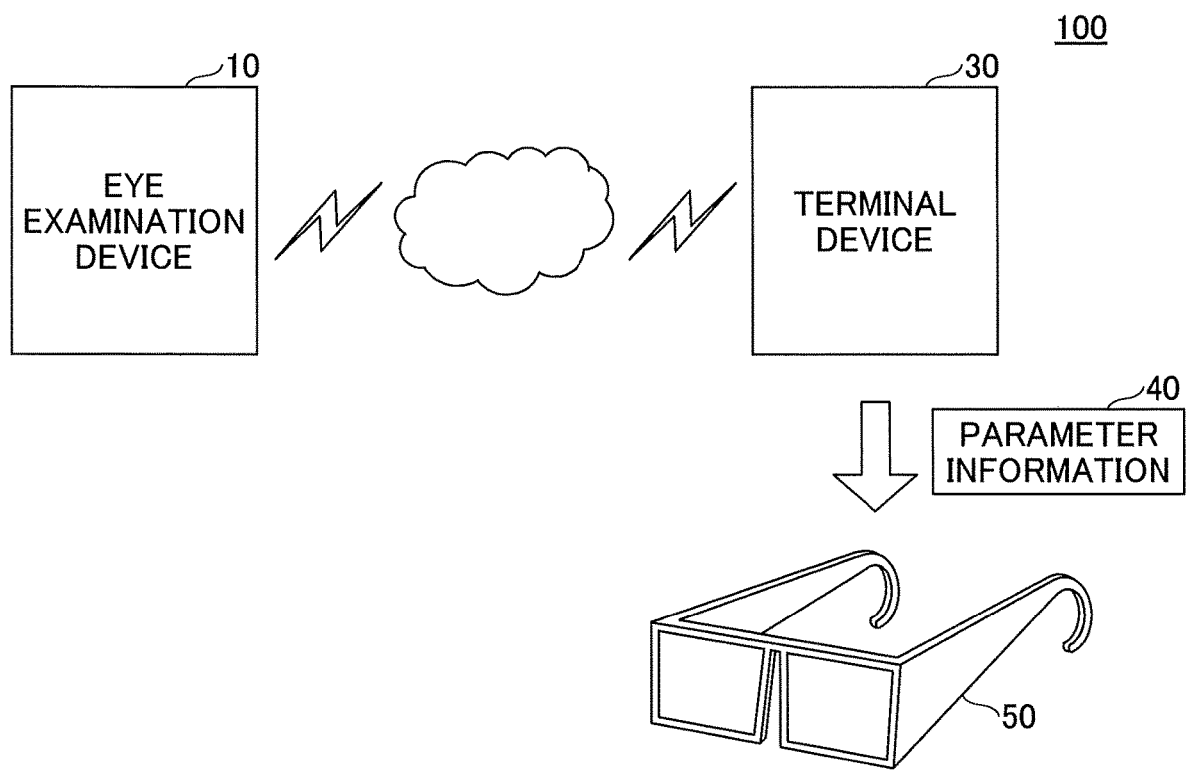
FIG. 2 is a diagram illustrating an example of a system configuration of an eyewear provision system according to the first embodiment.

Next, a retinal scanning type eyewear provision system using the eye examination device 10 according to the present embodiment will be described with reference to FIG. 2. In the following description, the retinal scanning type eyewear provision system is simply referred to as an eyewear provision system. FIG. 2 is a diagram illustrating an example of a system configuration of the eyewear provision system according to the first embodiment.

The eyewear provision system 100 according to the present embodiment includes the eye examination device 10 and a terminal device 30. The eye examination device 10 communicates with the terminal device 30 via a network or the like.

In the eyewear provision system 100 according to the present embodiment, when the eye examination device 10 acquires parameter information 40 of the subject P, the eye examination device 10 transmits the acquired parameter information 40 to the terminal device 30.

The terminal device 30 according to the present embodiment may be, for example, a terminal device for controlling a manufacturing device for manufacturing an eyewear 50. The eyewear 50 is a retinal scanning type head-mounted display. In this case, the terminal device 30 may read out the parameter information 40 during manufacturing process of the eyewear 50, and may cause the manufacturing device of the eyewear 50 to mount or set various parts on the eyewear 50 based on the parameter information 40.

The terminal device 30 according to the present embodiment may be, for example, a terminal device disposed in a shop selling the eyewear 50 which is used for storing and managing the parameter information 40 together with customer information. In this case, for example, when receiving an order for an eyewear 50, the terminal device 30 may pass the parameter information 40 of a user of the eyewear 50 to a manufacturing factory of the eyewear 50 or the like.

As described above, in the present embodiment, by only performing an eye examination of users, the parameter information necessary for customizing the eyewear 50 for each of the users can be obtained, and the obtained parameter information can be used for manufacturing the eyewear 50. Therefore, according to the present embodiment, manufacturing efficiency of the eyewear 50 can be improved.

Further, for example, the terminal device 30 according to the present embodiment may be a terminal device owned by the subject P who conducts an eye examination. Further, the terminal device 30 of the present embodiment may be a control device connected to the eyewear 50. As described here, if the user's parameter information 40 is stored in the terminal device or the eyewear 50 owned by the user, this parameter information can be used, for example, in a case of replacement or repair of the eyewear 50.

Figure 3:
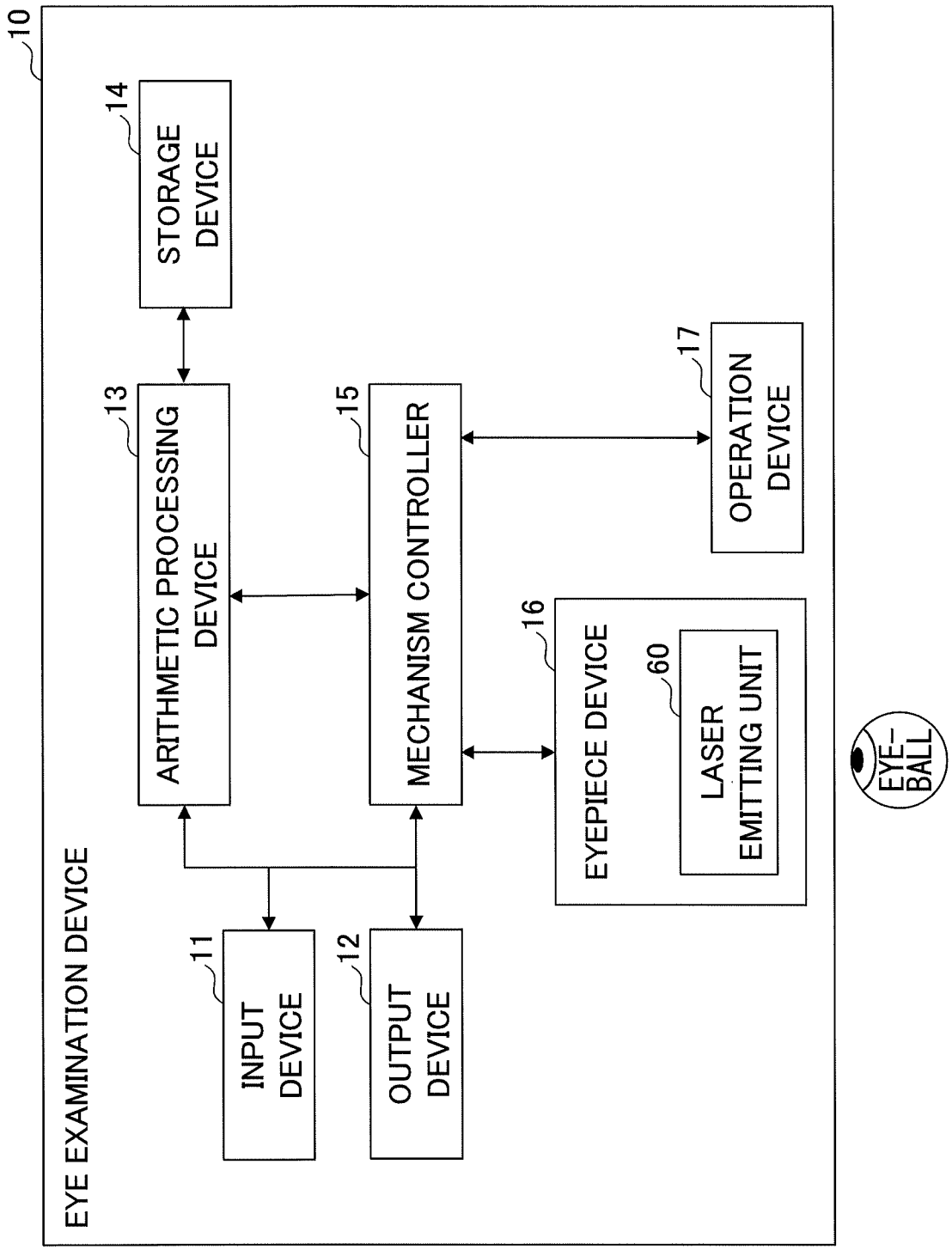
FIG. 3 is a diagram illustrating an example of a hardware configuration of an eye examination device.

Next, an eye examination device 10 according to the present embodiment will be described with reference to FIG. 3. FIG. 3 is a diagram illustrating an example of a hardware configuration of an eye examination device.

The eye examination device 10 according to the present embodiment includes an input device 11, an output device 12, an arithmetic processing device 13, a storage device 14, a mechanism controller 15, an eyepiece device 16, and an operation device 17.

The input device 11 receives various types of information with respect to the eye examination device 10. The input device 11 also includes, for example, an operating device or a keyboard that provides instructions to the eye examination device 10, and a receiving device that receives information transmitted to the eye examination device 10.

The output device 12 outputs various types of information from the eye examination device 10. The output device 12 also includes, for example, a transmission device that transmits information acquired by the eye examination device 10 to an external device, and a display that displays results of various processes performed by the eye examination device 10.

The arithmetic processing device 13 is implemented by a CPU (Central Processing Unit) or the like that controls an entirety of the eye examination device 10. The storage device 14 stores various programs executed in the arithmetic processing device 13, test image data, and the like. In addition, the storage device 14 retains the parameter information acquired as a result of the eye examination, the eye examination result information, and the like.

The mechanism controller 15 controls operations of various mechanisms in the eyepiece device 16 of the eye examination device 10, in response to manipulation of an operation device 17. The mechanism controller 15 also outputs the test image data read out from the storage device 14 by the arithmetic processing device 13 to the eyepiece device 16.

The eyepiece device 16 includes a laser emitting unit 60, and includes a mechanism for moving the laser emitting unit 60 to emit a laser beam emitted from the laser emitting unit 60 to a desired location of the subject. The laser emitting unit 60 emits laser light to project an image for examination (test image) onto a retina of the subject P, based on the image data for examination (test image data) input from the mechanism controller 15. Details of the eyepiece device 16 and the laser emitting unit 60 will be described below. The operation device 17 is manipulated to adjust a position of the laser emitting unit 60 in the eyepiece device 16.

Figure 4:
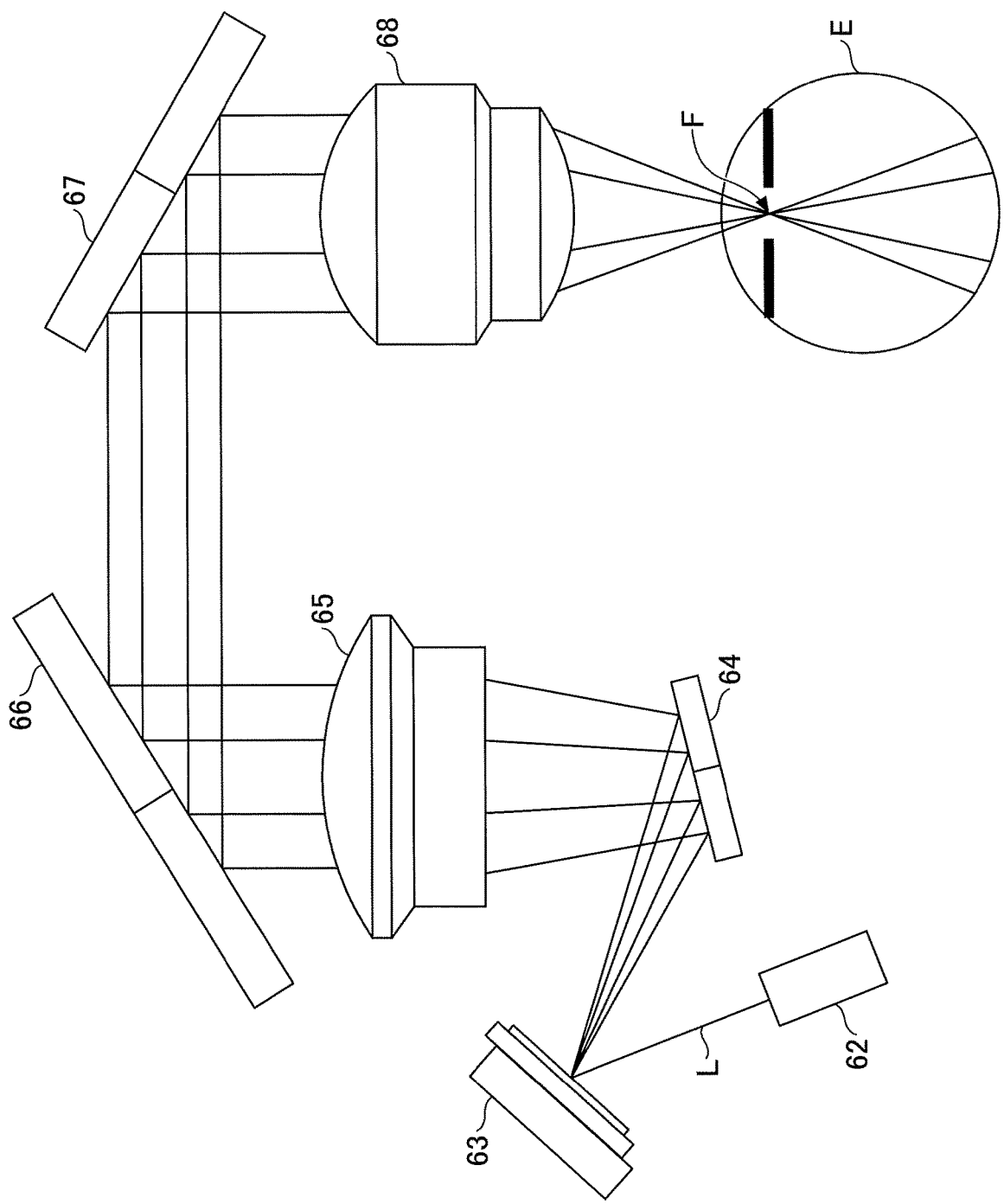
FIG. 4 is a diagram illustrating a configuration of a laser emitting unit.

Next, a configuration of the laser emitting unit 60 according to the present embodiment will be described with reference to FIG. 4. FIG. 4 is a diagram illustrating a configuration of the laser emitting unit.

The laser emitting unit 60 according to the present embodiment includes a laser light source 62, a MEMS (Micro Electro Mechanical Systems) mirror 63, a mirror 64, a tablet lens 65, a mirror 66, a mirror 67, and a condenser 68.

The laser light source 62 emits a laser beam L, based on the test image data, so that the test image is projected onto a retina of an eyeball E. The MEMS mirror 63 scans the laser beam L vertically and horizontally by control based on the test image data.

The laser beam L scanned by the MEMS mirror 63 is reflected by the mirror 64 and enters the tablet lens 65. A direction of the laser beam L passing through the tablet lens 65 is changed to a desired direction by the mirrors 66 and 67, and is entered into the condenser 68. That is, in the present embodiment, the laser beam L is condensed by the tablet lens 65 and the condenser 68, and is emitted from the laser emitting unit 60 toward the eyeball E of the subject P. At this time, the laser beam L is condensed to converge at a laser focal point F, which is the substantially central portion of a lens of the eyeball E. A distance from a surface of the condenser 68 on a side facing the eyeball E to the laser focal point F is usually set at approximately 5 mm to 7 mm.

FIG. 4 is an example of, but not limited to, an optical system of the laser emitting unit 60. The number and arrangement of mirrors and condensers may vary depending on configurations of the eyepiece device 16.

Next, an eyepiece device 16 according to the present embodiment will be described with reference to FIG. 5. FIG. 5 is a diagram illustrating a configuration of the eyepiece device. FIG. 5 (A) illustrates a perspective view of a right portion of the eyepiece device 16 divided at the center. FIG. 5 (B) illustrates a front view of FIG. 5 (A) when viewed from a direction of arrow A. FIG. 5 (C) illustrates a bottom view of FIG. 5 (A). A left portion of the eyepiece device 16 according to the present embodiment has the same configuration as that obtained by laterally inverting the configuration of the right portion.

The eyepiece device 16 according to the present embodiment includes the laser emitting unit 60, a base 70, an X-axis drive motor 71, a Y-axis drive motor 72, a Z-axis drive motor 73, an X-axis rotation motor 74, and a Y-axis rotation motor 75.

The laser emitting unit 60 is supported by the base 70 so as to be moved (translated) in the X-axis direction, the Y-axis direction, and the Z-axis direction illustrated in the drawing by the X-axis drive motor 71, the Y-axis drive motor 72, and the Z-axis drive motor 73 respectively. The laser emitting unit 60 is also supported by the base 70 so as to be rotated around the X-axis and the Y-axis illustrated in the drawing by the X-axis rotation motor 74 and the Y-axis rotation motor 75 respectively.

For example, when the X-axis drive motor 71, the Y-axis drive motor 72, and the Z-axis drive motor 73 are driven in response to manipulation of the operation device 17, the laser emitting unit 60 is moved in an X-axis direction, a Y-axis direction, and a Z-axis direction respectively. In addition, in response to manipulation of the operation device 17, the X-axis rotation motor 74 and the Y-axis rotation motor 75 are driven, and the laser emitting unit 60 rotates about the X-axis and the Y-axis respectively. The focal point F exists on a rotational axis in the X-axis direction (may be referred to as an X-rotational axis) and on a rotational axis in the Y-axis direction (may be referred to as a Y-rotational axis). That is, the laser focal point F exists at an intersection of the X-rotational axis and the Y-rotation axis, and the X-rotational axis and the Y-rotational axis rotate about the focal point F.

In the present embodiment, for example, a moving distance in the X-axis direction from an initial state, a moving distance in the Y-axis direction from the initial state, a moving distance in the Z-axis direction from the initial state, a rotation angle around the X-axis from the initial state, a rotation angle around the Y-axis from the initial state, and the like may be acquired as the parameter information.

That is, in the present embodiment, the rotation angles around the X-axis and the Y-axis with respect to the laser focal point F are parameter information.

The moving distance in the X-axis direction is used to calculate the pupil-to-pupil distance. Specifically, the sum of the moving distance in the X-axis direction and a moving distance in the X-axis direction of the left portion of the eyepiece device 16 is the pupil-to-pupil distance. Also, the Y-axis moving distance may vary, for example, depending on a position of the eye on the face of the subject P. In addition, the moving distance in the Z-axis direction may vary, for example, depending on shapes of the nose, the forehead, and a portion of the forehead between the eyebrows of the subject P.

Here, even if the laser emitting unit 60 is moved in the X-axis direction, the Y-axis direction, or the Z-axis direction, a distance from the surface of the condenser 68 on the side facing the eyeball E to the laser focal point F does not change.

Furthermore, the rotation angle around the X-axis and the rotation angle around the Y-axis may vary depending on condition of the eyelid and eyelash of the subject P and a position in the retina of the subject P on which the test image is projected.

When conducting an eye examination, the position of the laser emitting unit 60 is caused to be adjusted by the subject P so that the subject P can see the test image best. The subject P visually recognizes the test image when the laser beam emitted from the laser emitting unit 60 passes through the pupil of the subject P and is emitted onto the retina. Accordingly, in the present embodiment, by letting the subject P adjust the position of the laser emitting unit 60 in the eyepiece device 16 so as to see the test image best, the parameter information indicating an optimum positional relationship between the laser light source 62 and the eyeball of the subject P can be obtained.

In the eyewear provision system 100 according to the present embodiment, the positional relationship between the laser light source and the eyeball of the subject P indicated by the parameter information is reflected in a relationship between a laser light source of the eyewear and an eyeball of a user of the eyewear. That is, in the eyewear provision system 100 according to the present embodiment, by causing a user who is to use the eyewear to conduct an eye examination using the eye examination device 10 and thereby obtaining the parameter information of the user, the user's eyewear is customized by using this parameter information.

According to the present embodiment, by using the parameter information as described above, in the eyewear manufacturing process for example, complicated steps of causing a user to try on the eyewear, manually adjusting a position of a laser light source, and the like, can be omitted.

Figure 6:
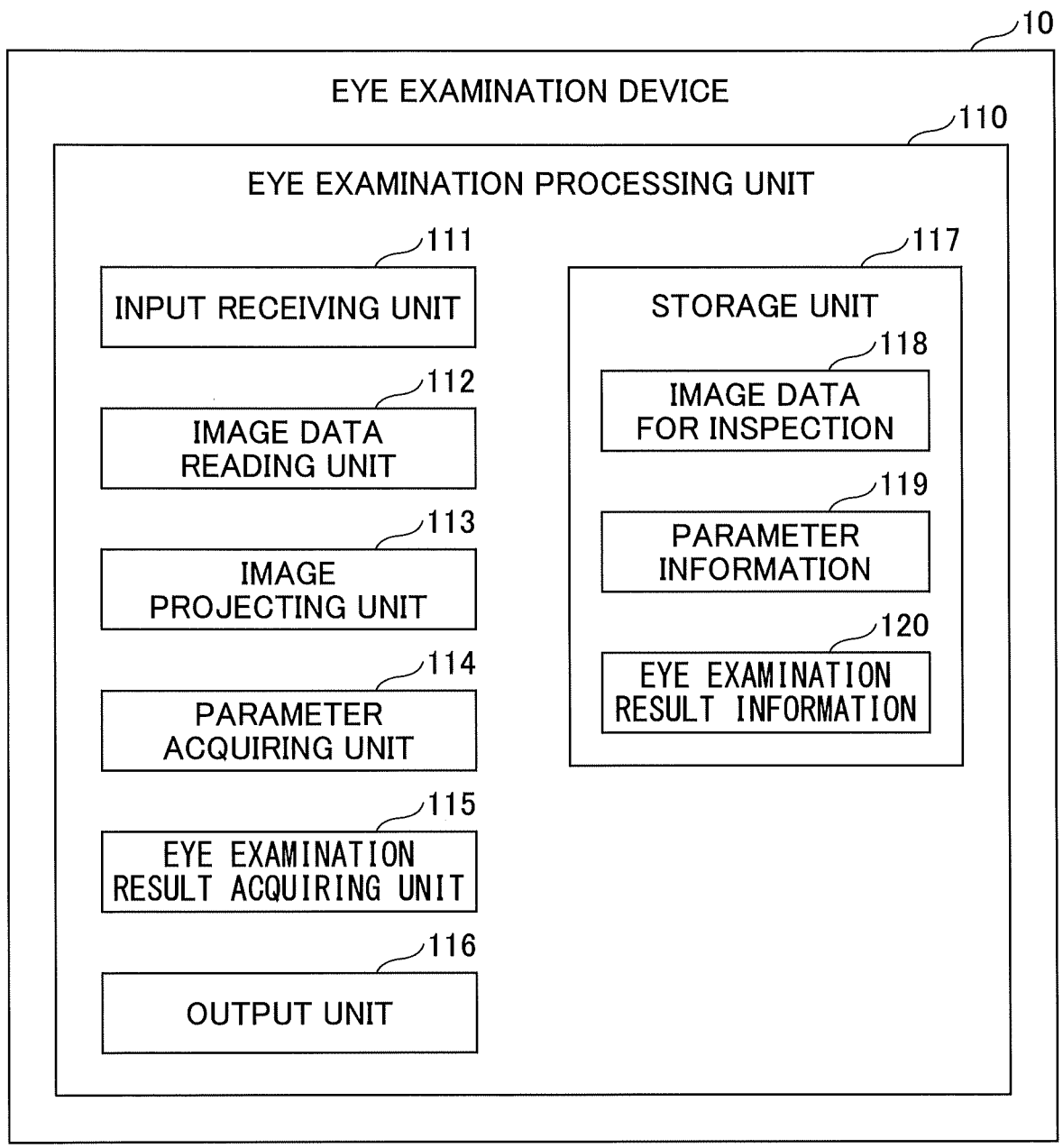
FIG. 6 is a diagram illustrating functions of the eye examination device.

Next, a functional configuration of the eye examination device 10 according to the present embodiment will be described with reference to FIG. 6. FIG. 6 is a diagram illustrating functions of the eye examination device.

The eye examination device 10 according to the present embodiment includes an eye examination processing unit 110. The eye examination processing unit 110 is embodied by the arithmetic processing device 13 reading out and executing a program stored in the storage device 14.

The eye examination processing unit 110 according to the present embodiment includes an input receiving unit 111, an image data reading unit 112, an image projecting unit 113, a parameter acquiring unit 114, an eye examination result acquiring unit 115, an output unit 116, and a storage unit 117.

The input receiving unit 111 receives various inputs directed to the eye examination device 10. Specifically, the input receiving unit 111 receives an eye examination start request to the eye examination device 10, an operating instruction from the operation device 17, and the like.

The image data reading unit 112 reads out the test image data stored in the storage unit 117. The image projecting unit 113 causes the laser emitting unit 60 to emit the laser beam L in accordance with the test image data that is read out, and projects the test image on the retina of the subject P.

The parameter acquiring unit 114 acquires parameter information of the eyepiece device 16 retained by the mechanism controller 15 according to an operation of the operation device 17.

The eye examination result acquiring unit 115 causes the test image to be projected onto the retina of the subject P, and acquires information indicating a result of the eye examination for the subject P.

A method of acquiring the eye examination result information by the eye examination result acquiring unit 115 will be described here. For example, the eye examination device 10 according to the present embodiment may display an image for examination (test image) on the output device (display) 12 and the like of the eye examination device 10, and let the subject P enter information of an area that the subject P could see. If it is difficult for the subject P to enter a result of the eye examination in a state of his/her eye being close to the eye examination device 10, it is possible to ask an examination assistant to enter the data into the eye examination device 10. In this case, for example, the subject P may read out a character visible to the subject P to inform the examination assistant of the area from which the character could be seen. In addition, if the eye examination device 10 has a voice input unit (microphone, etc.) and a speech recognition function, the result of the eye examination can be entered by the subject P reading out a character that the subject P could recognize.

The output unit 116 transmits the acquired parameter information to the terminal device 30. The output unit 116 may store, into the storage unit, eye examination information and the like that has been acquired.

The storage unit 117 is, for example, a storage area provided in the storage device 14, and stores the image data for inspection (test image data) 118, the parameter information 119, and the eye examination result information 120. The image data for inspection 118 may be stored in the storage unit 117 in advance. The parameter information 119 and the eye examination result information 120 may be temporarily retained after an eye examination is conducted.

Figure 7:
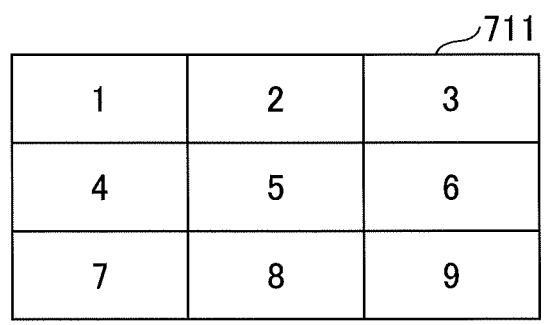
FIG. 7 is a diagram illustrating an example of a test image according to the first embodiment.

Next, information stored in the storage unit 117 will be described with reference to FIGS. 7 to 9. FIG. 7 is a diagram illustrating an example of the test image according to the first embodiment.

The test image 711 according to the present embodiment is projected to the retina of the subject P by a laser beam emitted based on the image data for inspection 118.

The test image 711 is divided into multiple regions, and an identifier is described in each of the regions to identify each of the regions. In the example of FIG. 7, the test image 711 is divided into nine regions, and an identifier is described in each of the regions to distinguish the regions.

In the present embodiment, for example, among identification numbers from 1 to 9 in the test image 711, if there is an identification number that a subject (examinee) cannot visually recognize, the subject is judged that a visual field defect occurs in a portion of his/her retina corresponding to the area specified by the identification number.

Although FIG. 7 illustrates a case in which the test image 711 is divided into nine regions, the test image 711 is not limited to this case. The test image 711 may be divided into regions of any number. Also, in FIG. 7, the test image 711 is divided into nine rectangular regions, but shapes of the regions are not limited thereto. The test image 711 may be divided into regions of any shape. Further, in FIG. 7, the identifier identifying each of the regions in the test image 711 is a number, but is not limited thereto. An identifier for identifying the region is not required to be a number, and a letter, an illustration, or the like may be used as an identifier.

The test image is not limited to the image illustrated in FIG. 7. For example, the test image may be a sandstorm image, Landolt rings, an ETDRS chart, an Amsler chart, or the like.

Figure 8:
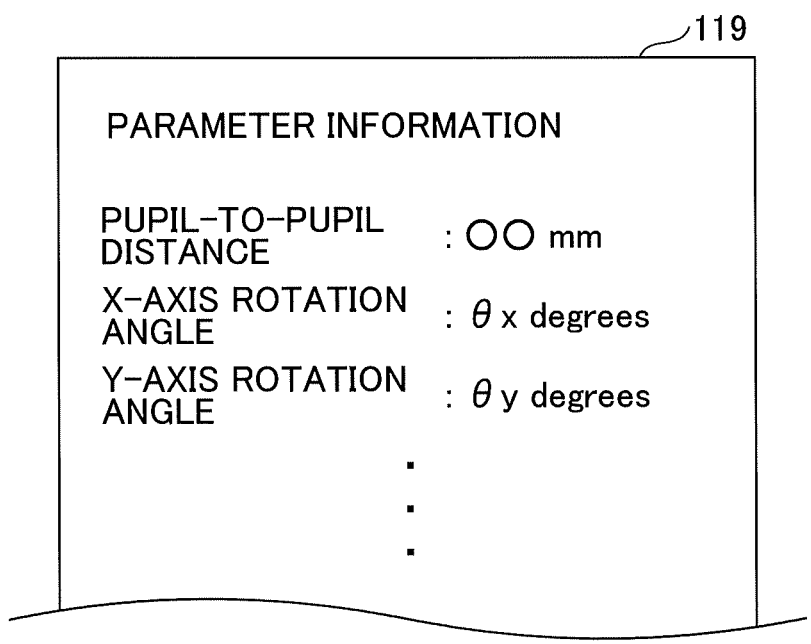
FIG. 8 is a diagram illustrating an example of parameter information of the first embodiment.

FIG. 8 is a diagram illustrating an example of parameter information of the first embodiment. The parameter information 119 of the present embodiment includes, for example, a pupil-to-pupil distance, a rotation angle about the X-axis, and a rotation angle about the Y-axis. Although not illustrated in FIG. 8, the respective moving distances in the X-axis direction, the Y-axis direction, and the Z-axis direction may also be included.

Figure 9:
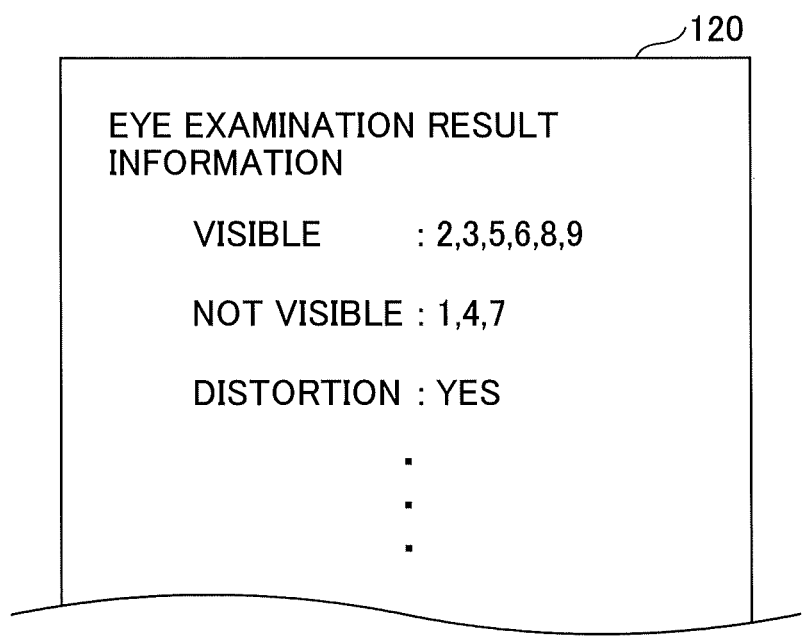
FIG. 9 is a diagram illustrating an example of eye examination result information of the first embodiment.

FIG. 9 is a diagram illustrating an example of the eye examination result information of the first embodiment. The eye examination result information 120 of the present embodiment includes, for example, identifiers of areas in the test image 711 that can be visually recognized by the subject P and identifiers of areas in the test image 711 that cannot be visually recognized by the subject P in the test image 711. In the present embodiment, these identifiers allow determination of presence or absence of a visual field defect in the subject P.

In the example of FIG. 9, identifiers of the areas that can be visually recognized by a subject P are "2, 3, 5, 6, 8, and 9", and identifiers of areas that cannot be visually recognized by the subject P are "1, 4, and 7". Thus, with respect to this subject P, a visual field defect occurs in an area corresponding to the regions whose identifiers are "1, 4, and 7".

In addition, the eye examination result information 120 may include, for example, a subjective symptom felt by the subject P. For example, the eye examination result information 120 in FIG. 9 shows that a visual field of the subject P is distorted.

Figure 10:
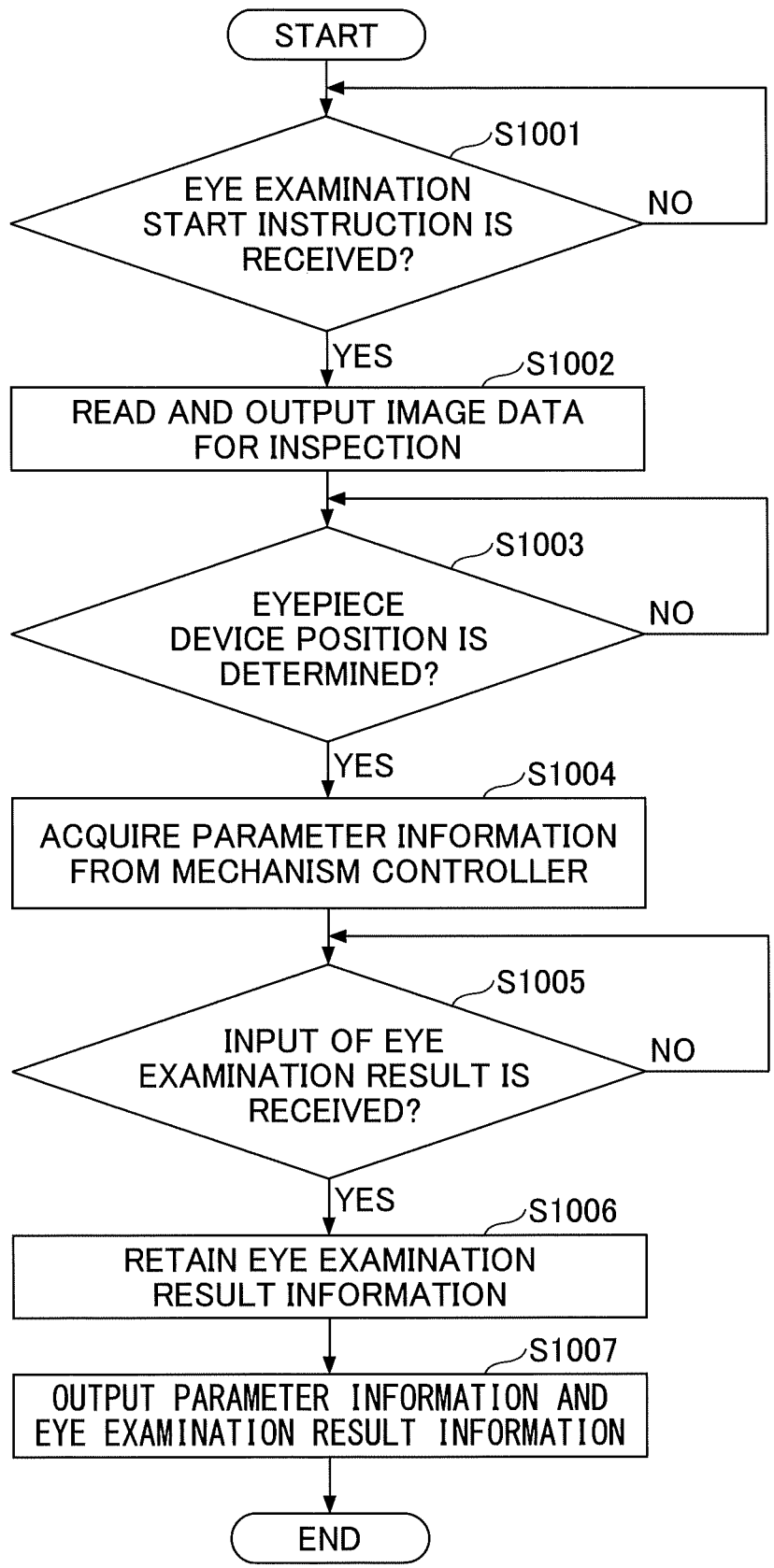
FIG. 10 is a flowchart illustrating a process of the eye examination device according to the first embodiment.

Next, an operation of the eye examination device 10 according to the present embodiment will be described with reference to FIG. 10. FIG. 10 is a flowchart illustrating a process of the eye examination device according to the first embodiment.

In the eye examination device 10 according to the present embodiment determines whether or not the input receiving unit 111 of the eye examination processing unit 110 has received an eye examination start instruction (step S1001). Specifically, the input receiving unit 111 may be deemed to have received the eye examination start instruction when a startup instruction of the eye examination device 10 is received.

In step S1001, when the eye examination start instruction is not received, the eye examination processing unit 110 waits until this instruction is received.

When the eye examination start instruction is received at step S1001, the eye examination processing unit 110 reads out the image data for inspection 118 from the storage unit 117, and causes the image projecting unit 113 to project the test image (step S1002).

Subsequently, the eye examination processing unit 110 determines whether or not a position of the laser emitting unit 60 in the eyepiece device 16 has been determined (step S1003). Specifically, the eye examination processing unit 110 determines whether or not the input receiving unit 111 has received a notification indicating that the position of the laser emitting unit 60 has been determined. In the present embodiment, for example, when adjustment of the position of the laser emitting unit 60 is completed, an operation for notifying that the adjustment is completed may be performed by using the operation device 17. Upon receiving this operation, the mechanism controller 15 may send a notification, to the arithmetic processing device 13, indicating that the position of the laser emitting unit 60 has been determined.

If the position is not determined at step S1003, the eye examination processing unit 110 waits until the position is determined. If the position has been determined at step S1003, the eye examination processing unit 110 causes the parameter acquiring unit 114 to acquire the parameter information 119 indicating the position of the laser emitting unit 60 in the eyepiece device 16 through the mechanism controller 15, and retains the parameter information 119 in the storage unit 117 (step S1004).

Next, the eye examination processing unit 110 determines whether or not an input of an eye examination result is received by the input receiving unit 111 (step S1005). If the input of the eye examination result is not received at step S1005, the eye examination processing unit 110 waits until the input of the eye examination result is received.

If the input of the eye examination result is received at step S1005, the eye examination processing unit 110 causes the eye examination result acquiring unit 115 to retain the result in the storage unit 117 as the eye examination result information 120 (step S1006).

Subsequently, the eye examination processing unit 110 causes the output unit 116 to transmit the acquired parameter information to the terminal device 30 (step S1007), and terminates the process. At this time, the output unit 116 may also transmit the eye examination result information 120 together with the parameter information 119 to the terminal device 30.

As described above, according to the present embodiment, the eye examination device 10 acquires parameter information indicating a positional relationship between an eyeball of a subject P and a laser light source, and based on the positional relationship indicated by the parameter information, an eyewear to be used for the subject P is manufactured. Accordingly, the present embodiment can contribute to improvement of manufacturing efficiency of the eyewear.

Second Embodiment

Hereinafter, a second embodiment will be described with reference to the drawings. In the second embodiment, the eye examination device 10 is connected with a management device that manages an eye examination by the eye examination device 10. In the following description of the second embodiment, an element having the same functional configuration as the first embodiment will be given the same symbol as that used in the description of the first embodiment, and the description thereof will be omitted.

Figure 11:
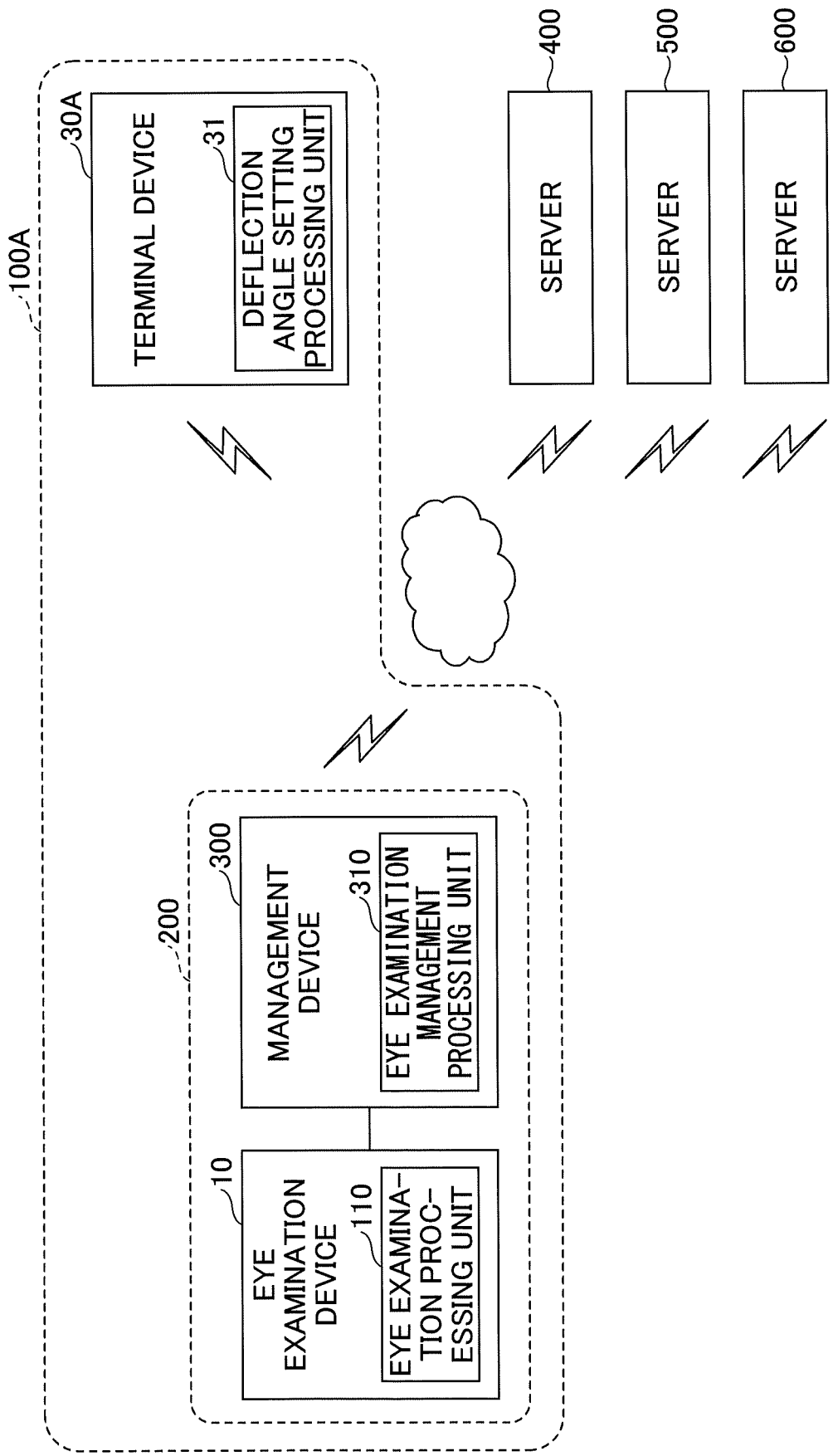
FIG. 11 is a diagram illustrating an example of a system configuration of an eyewear provision system according to a second embodiment.

FIG. 11 is a diagram illustrating an example of a system configuration of an eyewear provision system according to the second embodiment.

The eyewear provision system 100A according to the present embodiment includes the eye examination device 10, a management device 300, and a terminal device 30A. In the eyewear provision system 100A, the terminal device 30A and the management device 300 are connected with each other via a network or the like. Also, in the eyewear provision system 100A, the management device 300 and the eye examination device 10 are connected so as to satisfy respective communication standards.

In the present embodiment, the eye examination device 10 and the management device 300 are included in an eye examination system 200. In the example of FIG. 11, the number of the eye examination system 200 included in the eyewear provision system 100A is one, but is not limited to one. Any number of the eye examination systems 200 may be included in the eyewear provision system 100A.

In the eye examination system 200 according to the present embodiment, the eye examination device 10 outputs parameter information and eye examination result information to the management device 300.

In the eye examination system 200 according to the present embodiment, the management device 300 manages the eye examination result information and the parameter information in association with user information. Further, the management device 300 transmits the parameter information to the terminal device 30A.

In addition, the management device 300 according to the present embodiment includes an eye examination management processing unit 310. The eye examination management processing unit 310 maintains user information about a user who conducts an eye examination, and performs the eye examinations by using a test image in accordance with an attribute of the user.

Specifically, the eye examination management processing unit 310 identifies an external server from which the test image is acquired, according to the attribute of the user, and acquires contents provided by the identified external server as the test image. In the example illustrated in FIG. 11, the test image is to be obtained from one of servers 400, 500, and 600, as an external server.

In the eyewear provision system 100A according to the present embodiment, the terminal device 30A includes a deflection angle setting processing unit 31, and calculates and sets a deflection angle of a MEMS mirror installed in a light source unit of an eyewear, based on the parameter information received from the management device 300. The deflection angle of the MEMS mirror indicates an optical scan angle.

Figure 12:
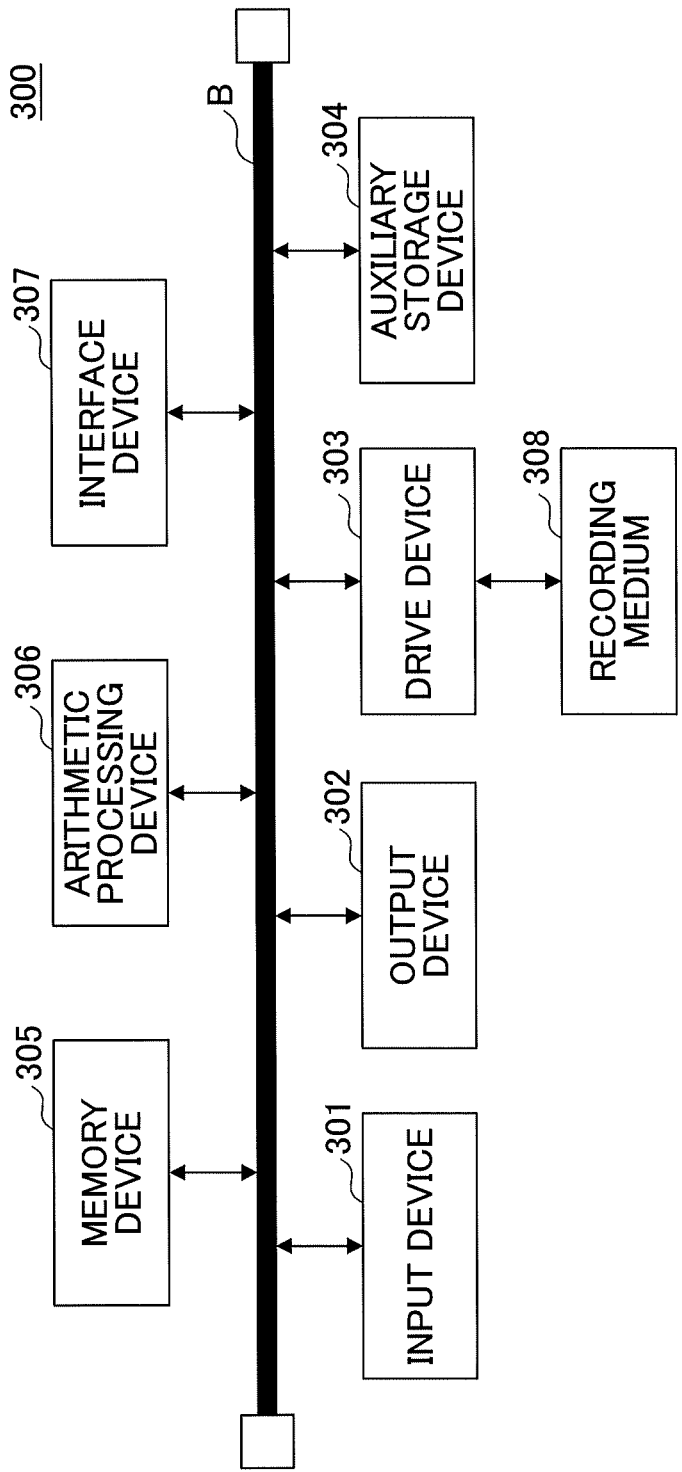
FIG. 12 is a diagram illustrating an example of a hardware configuration of a management device.

Hereinafter, a hardware configuration of the management device 300 according to the present embodiment will be described with reference to FIG. 12. FIG. 12 is a diagram illustrating an example of the hardware configuration of the management device.

The management device 300 according to the present embodiment includes an input device 301, an output device 302, a drive device 303, an auxiliary storage device 304, a memory device 305, an arithmetic processing device 306, and an interface device 307, each of which is interconnected via a bus B.

The input device 301 inputs various types of information. The output device 302 outputs various types of information. The interface device 307 includes a modem, a LAN card, or the like, and is used to connect to a network.

An eye examination management program is at least a part of various programs controlling the management device 300. The eye examination management program is provided, for example, by distribution of a recording medium 308 or by downloading from the network. As the recording medium 308 that stores the eye examination management program, various types of recording media can be used, such as a recording medium that optically, electrically, or magnetically records information, like a CD-ROM, a flexible disk, a magneto-optical disc, and the like, and a semiconductor memory that electrically records information, such as a ROM, a flash memory, and the like.

Also, when the recording medium 308 recording the eye examination management program is loaded in the drive device 303, the eye examination management program is installed into the auxiliary storage device 304 via the drive device 303 from the recording medium 308. The eye examination management program downloaded from the network is installed in the auxiliary storage device 304 via the interface device 307.

The auxiliary storage device 304 stores necessary files, data, and the like, in addition to storing the installed eye examination management program. The memory device 305 reads out and stores the eye examination management program from the auxiliary storage device 304 when starting up a computer. The arithmetic processing device 306 embodies various processes to be described below, in accordance with the eye examination management program stored in the memory device 305.

Because the terminal device 30A according to the present embodiment is a general computer and has the same configuration as the management device 300, the description thereof is omitted.

Next, with reference to FIG. 13, functional configurations of each device in the eyewear provision system 100A according to the present embodiment will be described.

Figure 13:
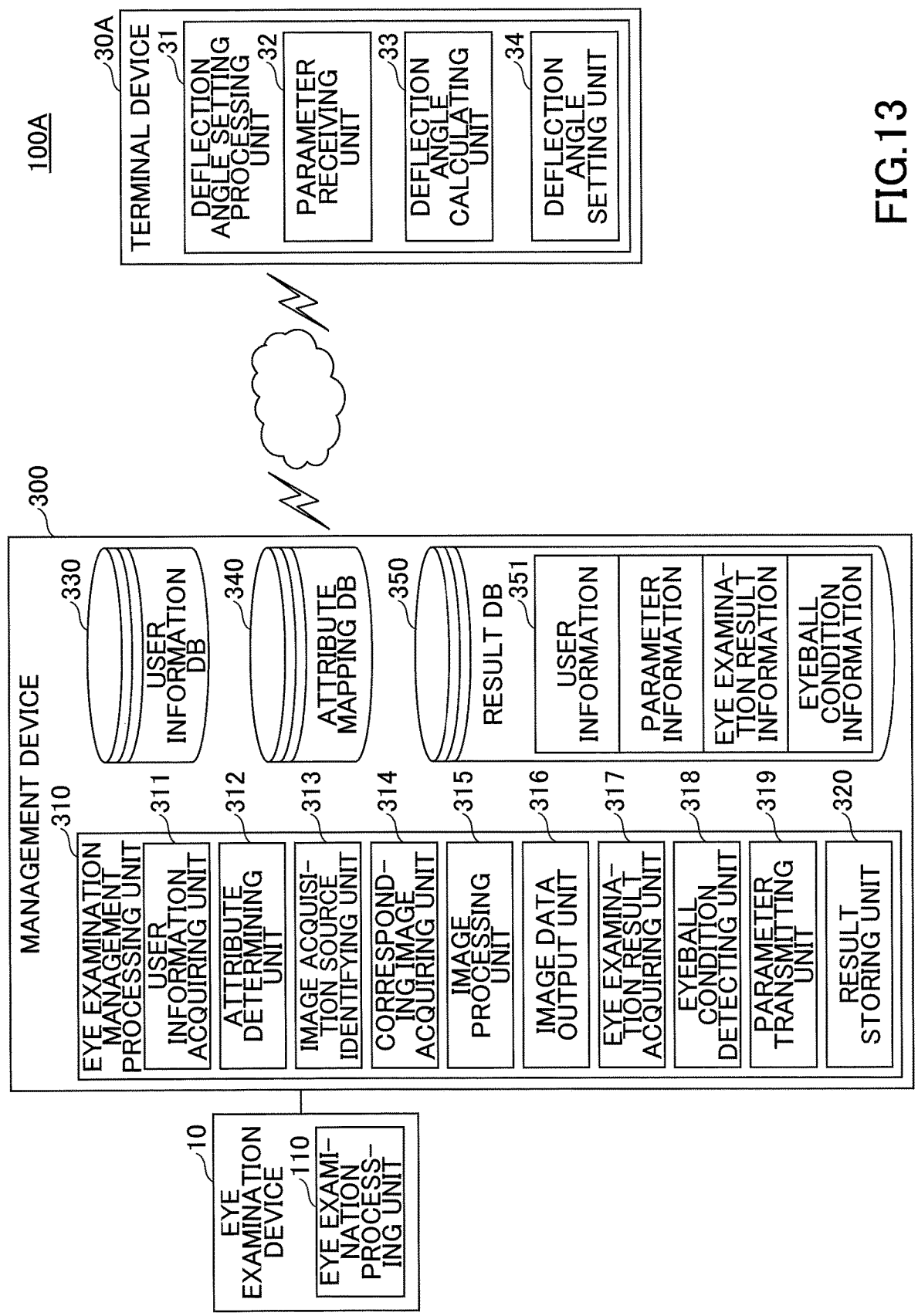
FIG. 13 is a diagram illustrating functions of each device in the eyewear provision system according to the second embodiment.

FIG. 13 is a diagram illustrating the functions of each device in the eyewear provision system according to the second embodiment.

First, functions of the management device 300 according to the present embodiment will be described. The management device 300 according to the present embodiment includes the eye examination management processing unit 310, a user information database 330, an attribute mapping database 340, and a result database 350.

The user information database 330 stores user information about a user who conducts an eye examination by using the eye examination device 10. The attribute mapping database 340 associates information indicating a user attribute with information indicating the server from which contents are to be retrieved. The result database 350 stores user information and an eye examination result, by correlating the user information with an eye examination result. Details of each of the databases in the management device 300 will be described below.

The eye examination management processing unit 310 according to the present embodiment is embodied by the arithmetic processing device 306 reading out and executing the eye examination management program stored in the memory device 305 or the like.

The eye examination management processing unit 310 according to the present embodiment includes a user information acquiring unit 311, an attribute determining unit 312, an image acquisition source identifying unit 313, a corresponding image acquiring unit 314, an image processing unit 315, an image data output unit 316, an eye examination result acquiring unit 317, an eyeball condition detecting unit 318, a parameter transmitting unit 319, and a result storing unit 320.

The user information acquiring unit 311 acquires user information. The user information may be received, for example, by the input receiving unit 111 in the eye examination device 10, and may be output to the management device 300. Alternatively, the user information may be input by using the input device 301 or the like in the management device 300. Details of the user information will be described below.

The attribute determining unit 312 determines an attribute of the user from information contained in the user information. The image acquisition source identifying unit 313 identifies an external server corresponding to the attribute of the user, by referring to the attribute mapping database 340.

The corresponding image acquiring unit 314 acquires image data of the contents provided by the server specified by the image acquisition source identifying unit 313. The image processing unit 315 processes the image data acquired by the corresponding image acquiring unit 314 to form the test image data. Details of a processing method performed by the image processing unit 315 will be described below.

The image data output unit 316 outputs the processed test image data to the eye examination device 10. The eye examination result acquiring unit 317 acquires the parameter information and the eye examination result information from the eye examination device 10.

The eyeball condition detecting unit 318 detects condition of an eyeball based on the eye examination result information, and outputs the condition as eyeball condition information. Specifically, the eyeball condition detecting unit 318 may retain reference information for determining condition of an eyeball, and may determine condition of an eyeball by comparing the eye examination result information with the reference information.

The parameter transmitting unit 319 transmits the parameter information obtained from the eye examination device 10 to the terminal device 30A. The result storing unit 320 stores the parameter information and the eye examination result information obtained by the eye examination result acquiring unit 317 and the eyeball condition information into the result database 350, in association with the user information.

Next, each of the databases in the management device 300 will be described. First, the result database 350 will be described.

The result database 350 according to the present embodiment stores result information 351 including the parameter information, the eye examination result information, and the eyeball condition information, in a manner in which the parameter information, the eye examination result information, and the eyeball condition information are associated with user information. The user information mentioned here is, for example, a user ID.

For example, in a case in which the user information of the result information 351 is a user ID of the subject P, the parameter information of the result information 351 is the parameter information 119 illustrated in FIG. 8, and the eye examination result information of the result information 351 is the eye examination result information 120 illustrated in FIG. 9.

In the eye examination result information 120, identifiers of areas that can be visually recognized by the subject P are "2, 3, 5, 6, 8, and 9", and identifiers of areas that cannot be visually recognized by the subject P are "1, 4, and 7" (see FIG. 9). Accordingly, the eyeball condition detecting unit 318 determines that there is a visual field defect. In addition, if the eyeball condition detecting unit 318 retains the reference information stating that "if there is a visual field defect in a peripheral area of the test image=possibility of glaucoma", the eyeball condition detecting unit 318 determines that there is a possibility of glaucoma with respect to the condition of the eyeball of the subject P. Therefore, in this case, the eyeball condition information will be "visual field defect is found/possibility of glaucoma".

In the present embodiment, the eyeball condition detecting unit 318 is provided in the management device 300, but is not limited thereto. The eyeball condition detecting unit 318 may be provided in the eye examination device 10. In this case, the eye examination device 10 may transmit parameter information, eye examination result information, and eyeball condition information to the management device 300.

Next, functions of the terminal device 30A according to the present embodiment will be described.

The terminal device 30A according to the present embodiment includes a deflection angle setting processing unit 31. The deflection angle setting processing unit 31 according to the present embodiment is embodied by an arithmetic processing device of the terminal device 30A reading out and executing a mirror control program stored in its storage device.

The deflection angle setting processing unit 31 according to the present embodiment includes a parameter receiving unit 32, a deflection angle calculating unit 33, and a deflection angle setting unit 34.

The parameter receiving unit 32 acquires the parameter information transmitted from the management device 300. The deflection angle calculating unit 33 determines a visually recognizable area on a retina of a user having conducted an eye examination, based on the parameter information. The deflection angle calculating unit 33 calculates a deflection angle of the MEMS mirror installed in the eyewear 50, based on the obtained area.

The deflection angle setting processing unit 31 according to the present embodiment may retain various types of information used for calculating the deflection angle, such as specification information indicating a specification of the MEMS mirror of the eyewear 50.

The deflection angle setting unit 34 sets the deflection angle calculated by the deflection angle calculating unit 33 to the eyewear 50.

Figure 14:
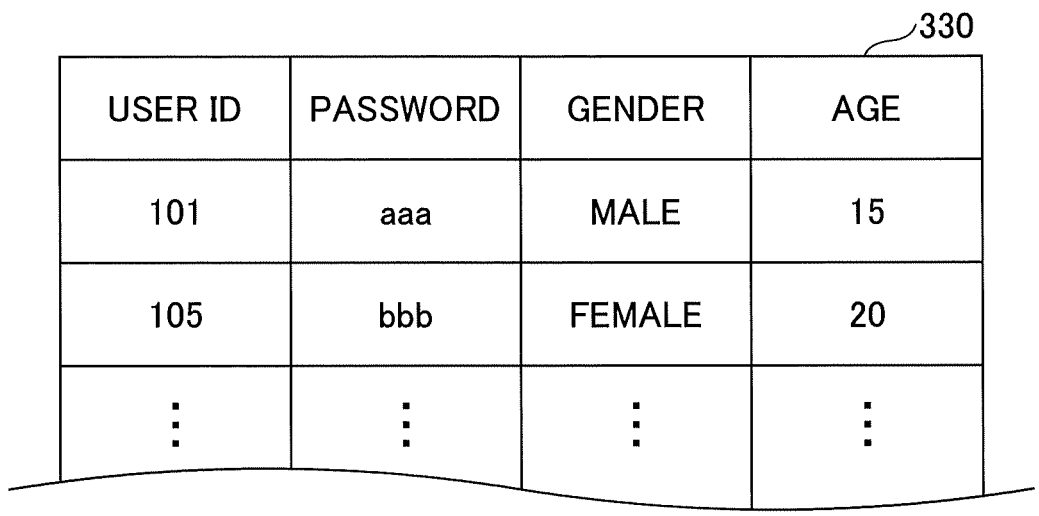
FIG. 14 is a diagram illustrating an example of a user information database according to the second embodiment.

Next, the user information database 330 and the attribute mapping database 340 of the present embodiment will be described with reference to FIGS. 14 and 15. FIG. 14 is a diagram illustrating an example of the user information database according to the second embodiment.

The user information database 330 according to the present embodiment includes, as items of information, a user ID, a password, gender, and an age. A value of the item "user ID" indicates an identifier for identifying a user of the eyewear provision system 100A. A value of the item "password" is the user's password identified by the user ID. A value of the item "gender" indicates the user's sex, and a value of the item "age" indicates the user's age. In the user information database 330, the item "user ID" and the other items are associated with each other, and the user information of the present embodiment is information including the value of the item "user ID" and the value of other items.

In the present embodiment, the value of the item "gender" and the value of the item "age" are used as information indicating the attributes of the user. The information indicating the attributes of the user is not limited to the items illustrated in FIG. 14. Information indicating user attributes may include, for example, items indicating user preferences.

Figure 15:
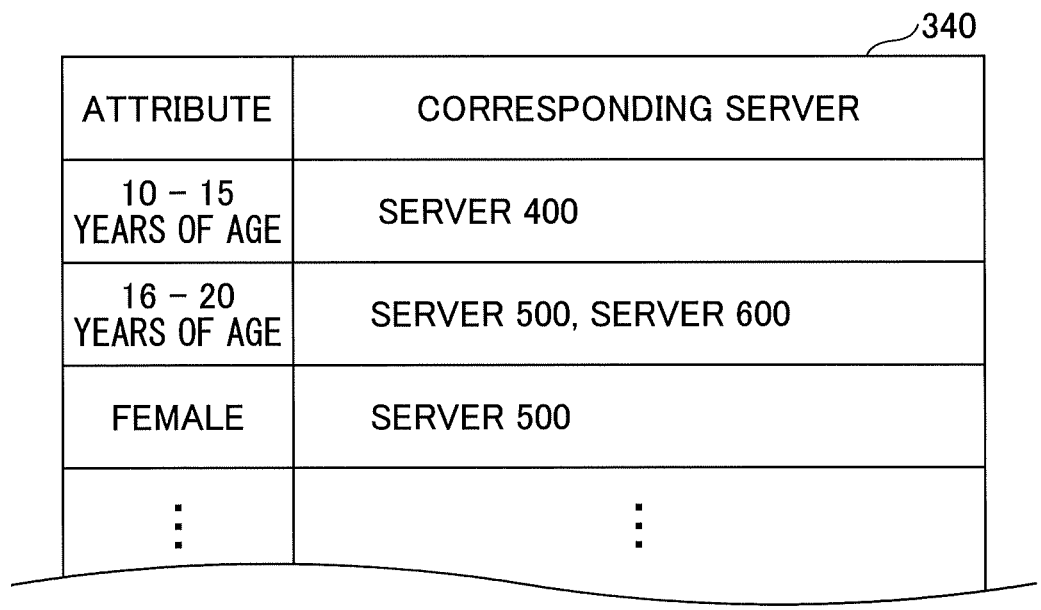
FIG. 15 is a diagram illustrating an example of an attribute mapping database according to the second embodiment.

FIG. 15 is a diagram illustrating an example of the attribute mapping database of the second embodiment. The attribute mapping database 340 according to the present embodiment includes, as items of information, an attribute and a corresponding server, and an item "attribute" and an item "corresponding server" are associated with each other.

The value of the item "attribute" is information indicating the attribute in the user information database 330. The value of the item "corresponding server" indicates information that identifies a server(s) associated with the attribute. Specifically, the value of the item "corresponding server" may be a name of a server, or may be a URL (Uniform Resource Locator) or the like identifying a server.

In FIG. 15, for example, if the attribute of the user is "female", a corresponding server is found to be the server 500. In this case, the corresponding image acquiring unit 314 accesses the server 500 to acquire image data provided by the server 500. The image data provided herein may be, for example, an advertisement image of a product for a woman. For example, if an age of a user is 10 or less, an image suitable for children may be used as the test image.

In the present embodiment, because an image corresponding to an attribute of a user is used as the test image, the user can conduct an eye examination with interest.

Next, image processing performed by the image processing unit 315 in the eye examination management processing unit 310 according to the present embodiment will be described with reference to FIG. 16. FIG. 16 is a diagram illustrating the image processing according to the second embodiment. An image 161 in FIG. 16 is an example of an image projected by image data before the image processing, and an image 161-1 is an example of an image projected by image data after the image processing.

The image 161 illustrated in FIG. 16 is an image of contents acquired from a server identified based on the attribute mapping database 340.

The image processing unit 315 according to the present embodiment applies image processing to the image of contents to a degree that the meaning of the content does not change. In the example illustrated in FIG. 16, a black frame 162 is superimposed on an outer periphery of the image 161 to form the test image 161-1.

In the present embodiment, by applying image processing to image data, a user conducting an eye examination with the eye examination device 10 is, for example, more likely to notice a visual field defect at the outer peripheral portion of the visual field.

A method of image processing performed by the image processing unit 315 is not limited to the method illustrated in FIG. 16. For example, the image processing unit 315 may change color of an image representing the contents, or may change color density of an image. In addition, the image processing unit 315 may superimpose on an image representing contents, for example, a grid pattern or the like by which the image representing the contents is divided into multiple areas.

As described above, by applying image processing to an image by the image processing unit 315, the visibility of the image can be enhanced even for a subject with eye disease such as retinopathy, and by reflecting the information in the user attribute database 330, versatility is enhanced.

In the example of FIG. 16, an image of contents acquired from a server is a still image, but it is not limited thereto. An image of contents acquired from a server may be, for example, a video.

Figure 17:
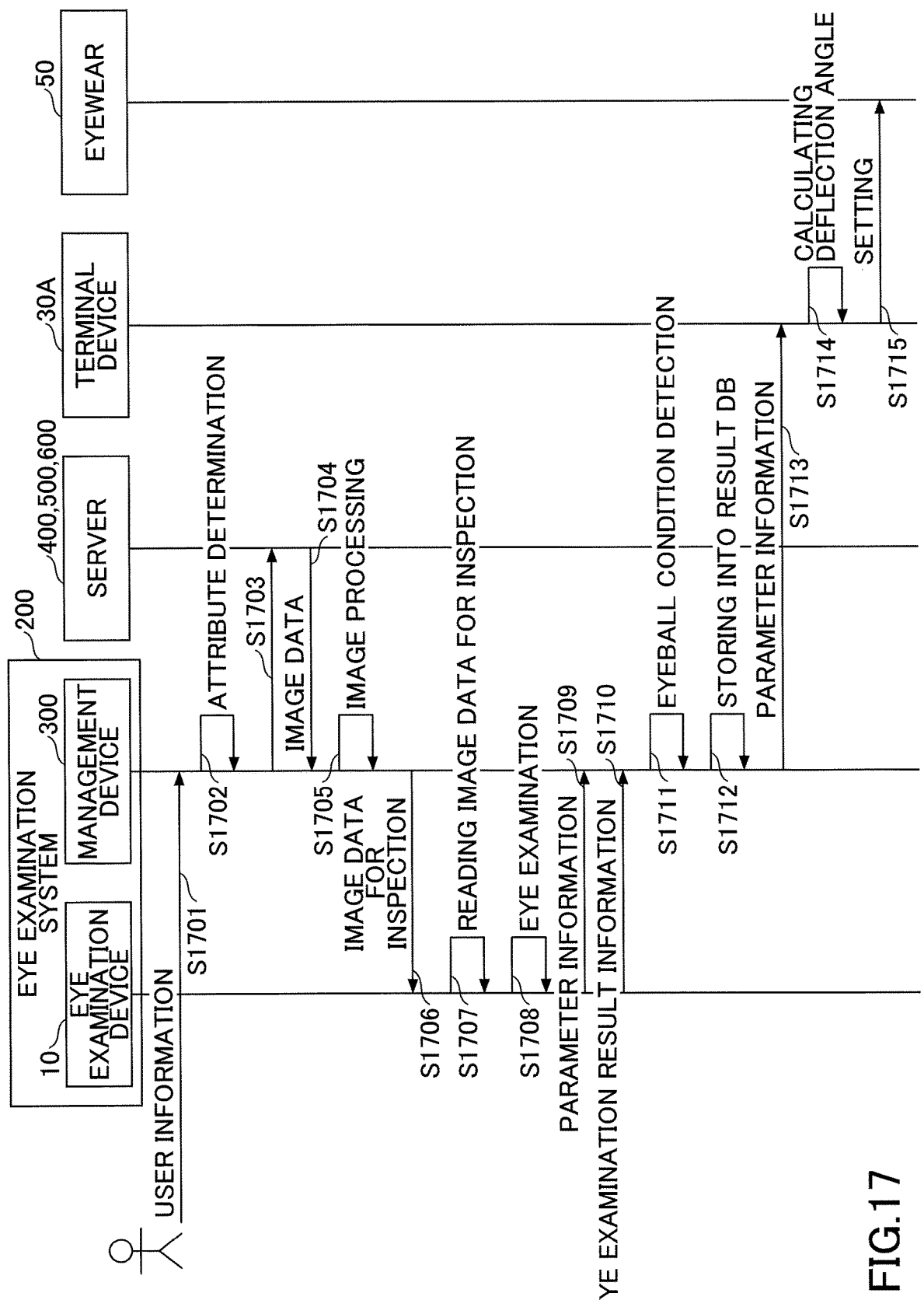
FIG. 17 is a sequence diagram illustrating an operation of the eyewear provision system according to the second embodiment.

Next, an operation of the eyewear provision system 100A according to the present embodiment will be described with reference to FIG. 17. FIG. 17 is a sequence diagram illustrating the operation of the eyewear provision system according to the second embodiment.

In the eyewear provision system 100A according to the present embodiment, when the management device 300 acquires the user information (step S1701), the management device 300 determines an attribute(s) of a user based on the user's user information, and identifies a server from which image data is to be acquired (step S1702).

Subsequently, the management device 300 issues an acquisition request of image data to the specified server (step S1703).

Subsequently, the server having received the notification transmits image data to the management device 300 in response to the acquisition request (step S1704). With respect to the aforementioned image data to be transmitted to the management device 300, for example, the server may determine image data to be supplied in advance.

Subsequently, the management device 300 processes the acquired image data (step S1705), and outputs, as the test image data, the processed image data to the eye examination device 10 (step S1706).

The eye examination device 10 reads the acquired test image data (step S1707), and projects the test image to perform an eye examination (step S1708). Subsequently, the eye examination device 10 outputs parameter information and eye examination result information to the management device 300 (step S1709 and step S1710).

When the management device 300 acquires the eye examination result information, the management device 300 detects condition of an eyeball (step S1711). Subsequently, the management device 300 stores the parameter information, the eye examination result information, and the eyeball condition information into the result database 350 in association with the user information (step S1712). Next, the management device 300 transmits the parameter information to the terminal device 30A (step S1713).

When the parameter information is received, the terminal device 30A calculates a deflection angle based on the parameter information (step S1714). Subsequently, the terminal device 30A sets the calculated deflection angle to the eyewear 50 (step S1715).

As described above, according to the eyewear provision system 100A of the present embodiment, the parameter information of the user who conducted the eye examination using the eye examination device 10 can be set to the eyewear 50, and the eyewear 50 can be provided to the user.

In other words, in the eyewear provision system 100A according to the present embodiment, when the management device 300 receives an input of user information, the management device 300 determines an attribute of a user of the eye examination device 10 based on the user information, and an eye examination is performed by using a test image according to the user. The eyewear provision system 100A according to the present embodiment retains the user's eye examination result information and parameter information in the management device 300, and the management device 300 transmits the parameter information from the management device 300 to the terminal device 30A. The terminal device 30A sets the received parameter information to the eyewear 50. The terminal device 30A of the present embodiment, which sets the parameter information to the eyewear 50, may be a terminal device that controls a manufacturing device for manufacturing the eyewear 50.

As described above, according to the eyewear provision system 100A of the present embodiment, parameter information of a user who conducted the eye examination can be set to an eyewear 50, to produce a user-specific eyewear 50 and to provide the eyewear 50 to the user.

Here, a use case of the eyewear provision system 100A according to the present embodiment will be described. In the following example, the eye examination system 200 including the eye examination device 10 and the management device 300 is installed at an eyewear shop, and a terminal device 30A, which serves as a terminal device for controlling an eyewear manufacturing apparatus, is installed in a manufacturing factory or the like for an eyewear 50.

In the use case, when a user visiting an eyewear shop purchases his/her own eyewear, the user first conducts an eye examination using the eye examination system 200 installed at the shop. After the eye examination is conducted by the user, the eye examination system 200 retains the parameter information and the eye examination result information in the management device 300, in association with user information of the user. In this case, the user information may include information for identifying the shop at which the eye examination system 200 is installed.

Next, the eye examination system 200 transmits, from the management device 300, the parameter information together with the user information to the terminal device 30A. In a manufacturing process of an eyewear, the terminal device 30A causes the manufacturing apparatus to fit the laser emitting unit 60 to the eyewear based on the received parameter information.

The eyewear manufactured here is to be purchased by the user identified by the user information. Thus, the eyewear is delivered from the manufacturing factory to the shop, and is delivered to the user at the shop.

According to the present embodiment, eyewear can be provided to a user who has conducted an eye examination as described above. Therefore, according to the present embodiment, it is possible to eliminate burdens of various adjustments to customize an eyewear to a user, by trial fitting of the eyewear to the user.

Figure 18:
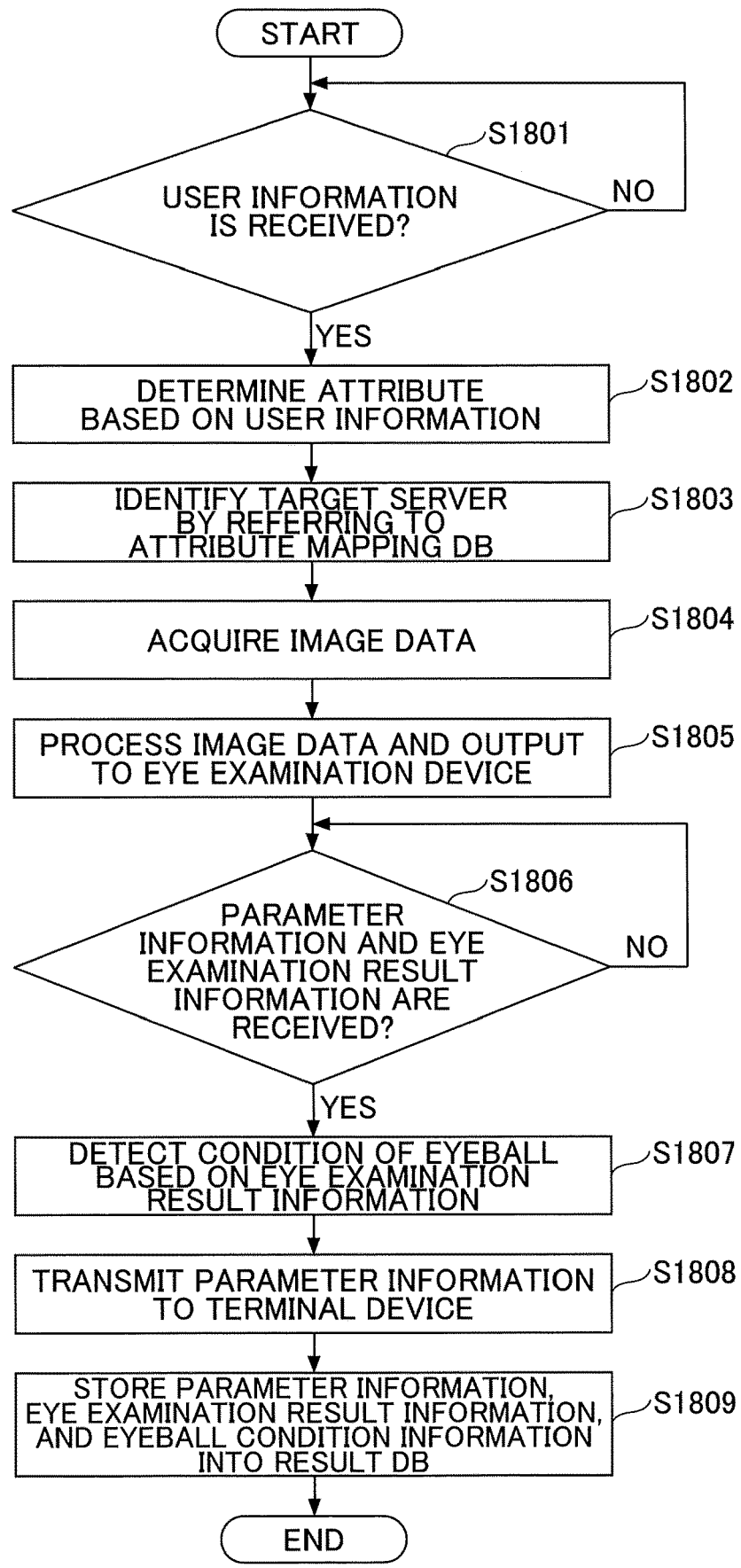
FIG. 18 is a flowchart illustrating a process of the management device according to the second embodiment.

Next, an operation of the management device 300 according to the present embodiment will be described with reference to FIG. 18. FIG. 18 is a flowchart illustrating a process of the management device according to the second embodiment.

The eye examination management processing unit 310 of the management device 300 according to the present embodiment determines whether or not the user information is received by the user information acquiring unit 311 (step S1801). If the user information is not acquired at step S1801, the eye examination management processing unit 310 waits until the user information is acquired.

If the user information is received at step S1801, the eye examination management processing unit 310 determines, by the attribute determining unit 312, an attribute of the user, from the values of the items "gender" and "age" included in the user information (step S1802).

Next, the eye examination management processing unit 310 causes the image acquisition source identifying unit 313 to identify the server corresponding to the attribute of the user by referring to the attribute mapping database 340 (step S1803). Subsequently, the eye examination management processing unit 310 causes the corresponding image acquiring unit 314 to acquire image data from the identified server (step S1804). Next, the eye examination management processing unit 310 obtains test image data by causing the image processing unit 315 to process the acquired image data, and causes the image data output unit 316 to output the test image data to the eye examination device 10 (step S1805).

Next, the eye examination management processing unit 310 determines whether or not the parameter information and the eye examination result information were acquired from the eye examination device 10 by the eye examination result acquiring unit 317 (step S1806). If the relevant information is not acquired at step S1806, the eye examination management processing unit 310 waits until the information is acquired.

If the relevant information is obtained at step S1806, the eye examination management processing unit 310 causes the eyeball condition detecting unit 318 to detect condition of the eyeball from the eye examination result information and to output the eyeball condition information (Step S1807).

Subsequently, the eye examination management processing unit 310 causes the parameter transmitting unit 319 to transmit the parameter information to the terminal device 30A (step S1808). Next, the eye examination management processing unit 310 causes the result storing unit 320 to store the parameter information, the eye examination result information, and the eyeball condition information in the result database 350 in association with the user information (step S1809), and terminates the process.

In the present embodiment, the eye examination management processing unit 310 obtains the test image data by causing the image processing unit 315 to apply image processing to the image data acquired by the corresponding image acquiring unit 314, but the present embodiment is not limited thereto. The eye examination management processing unit 310 may output the image data acquired by the corresponding image acquiring unit 314 directly to the eye examination device 10 as test image data.

Figure 19:
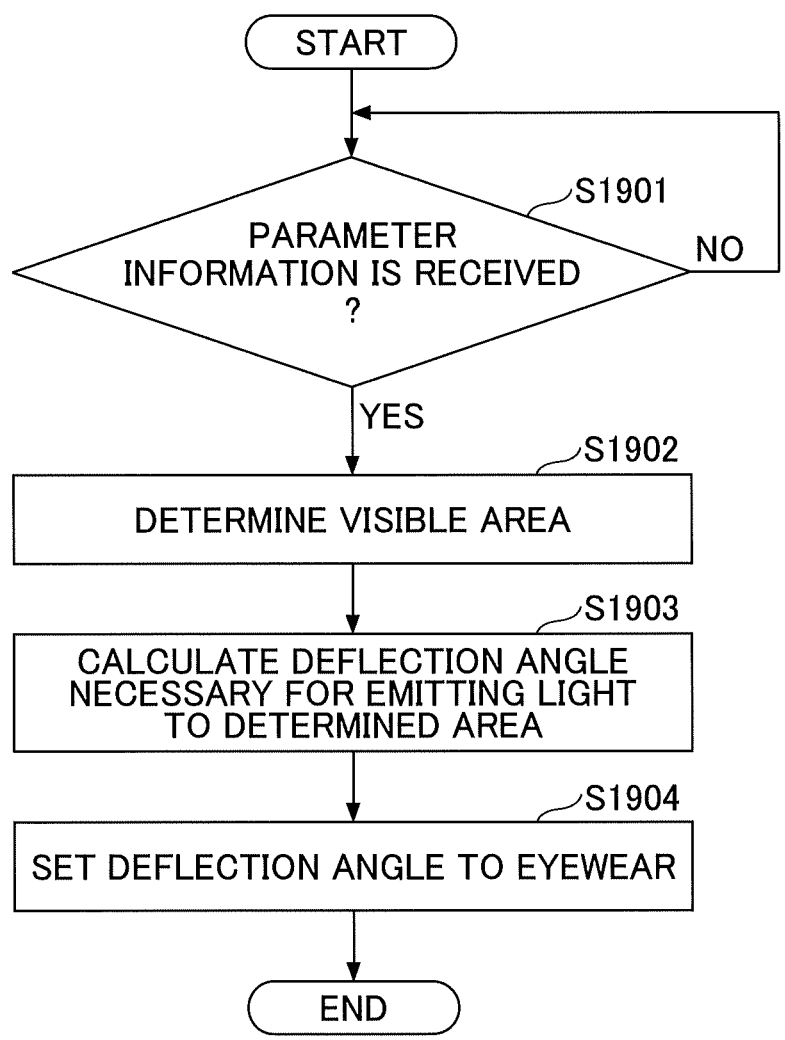
FIG. 19 is a flowchart illustrating a process of a terminal device according to the second embodiment.

Next, an operation of the terminal device 30A according to the present embodiment will be described with reference to FIG. 19. FIG. 19 is a flowchart illustrating a process of the terminal device according to the second embodiment.

The deflection angle setting processing unit 31 of the terminal device 30A according to the present embodiment determines whether or not the parameter information is received from the management device 300 by the parameter receiving unit 32 (step S1901). If the parameter information is not received at step S1901, the deflection angle setting processing unit 31 waits until the parameter information is received.

If the parameter information is received at step S1901, the deflection angle setting processing unit 31 causes the deflection angle calculating unit 33 to determine, based on the parameter information, an area representing a visual field of the user corresponding to the parameter information (step S1902). Specifically, for example, the deflection angle calculating unit 33 derives the area in which the laser emitting unit 60 in the eyepiece device 16 has scanned a laser beam, from the rotation angle around the X-axis in the eyepiece device 16, the rotation angle around the Y-axis in the eyepiece device 16, and the deflection angle of the MEMS mirror 63 in the laser emitting unit 60.

Next, based on the area derived at step S1902, the deflection angle calculating unit 33 calculates a deflection angle of a MEMS mirror in the eyewear 50 (step S1903). At this time, the deflection angle setting processing unit 31 may transmit the calculated deflection angle to the management device 300, in a state in which the calculated deflection angle is associated with user information (user ID) of the user. The management device 300 may store the received deflection angle in association with the corresponding user information in the result database 350.

Subsequently, the deflection angle setting processing unit 31 sets the calculated deflection angle to the eyewear 50 by using the deflection angle setting unit 34 (step S1904), and terminates the process. Specifically, the deflection angle setting unit 34 transmits the calculated deflection angle to a controller in the eyewear 50. The controller in the eyewear 50 sends the deflection angle to a drive controller that controls driving of the MEMS mirror of the eyewear 50, to cause the drive controller to set the deflection angle.

In the present embodiment, a laser beam is emitted to an area based on a user's visual field. For example, in a case in which a visual field defect exists in a user's eye, the laser beam is not emitted to an area corresponding to the defect. Thus, the eyewear 50 can reduce waste of electric power corresponding to the area irradiated with the laser beam.

In the present embodiment, the deflection angle setting processing unit 31 is, but not limited to, provided in the terminal device 30A to calculate the deflection angle. The deflection angle setting processing unit 31 may be, for example, provided in the management device 300, or may be provided in the eye examination device 10.

As described above, in the present embodiment, based on the parameter information, the eyewear 50 to be delivered to the user can be automatically configured to an extent that a laser beam can scan an area corresponding to a user's visual field. Accordingly, in the present embodiment, procedures for manufacturing and selling the eyewear 50 can be simplified, thereby contributing to improvement in manufacturing efficiency.

Further, according to the present embodiment, because an advertisement image corresponding to an attribute of a user is acquired as a test image, an eye examination can be conducted, for example, while providing information related to matters in which the user is likely to have interest.

Also, in the present embodiment, condition of a user's eyeball is detected from the eye examination result information, and the eyeball condition information is retained associated with user information of the user. Thus, according to the present embodiment, a user who conducts an eye examination can check condition of his/her own eyeball by a simple eye examination. Further, in the present embodiment, for example, in a case in which a user who has conducted an eye examination visits a medical institution, it is possible to provide the eye examination result information and the eyeball condition information to the user.

Third Embodiment

Hereinafter, a third embodiment will be described with reference to the drawings. The third embodiment differs from the second embodiment in that the management device is placed on a network. In the following description of the third embodiment, only differences from the second embodiment will be described, and for an element having the same functional configuration as the second embodiment, a symbol similar to that used in the description of the second embodiment is given, and the description thereof will be omitted.

Figure 20:
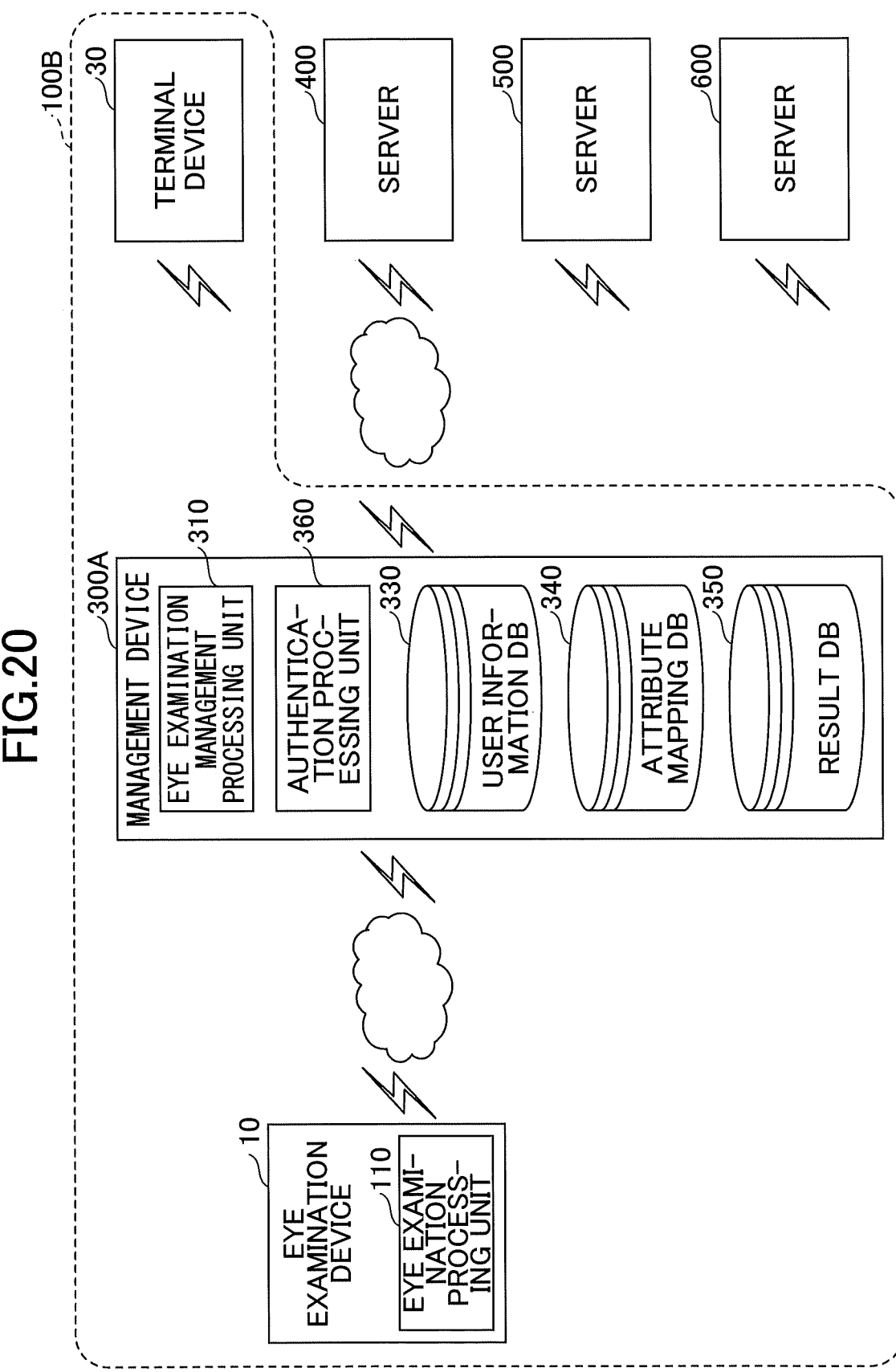
FIG. 20 is a diagram illustrating an example of a system configuration of an eyewear provision system according to a third embodiment.

FIG. 20 is a diagram illustrating an example of a system configuration of an eyewear provision system according to the third embodiment.

The eyewear provision system 100B according to the present embodiment includes the eye examination device 10, a management device 300A, and the terminal device 30. Note that the eyewear provision system 100B may include the terminal device 30A.

Each of the eye examination device 10 and the terminal device 30 is connected to the management device 300A via a network. The management device 300A is, for example, a server apparatus disposed in the cloud.

The management device 300A according to the present embodiment includes the eye examination management processing unit 310, the user information database 330, the attribute mapping database 340, the result database 350, and an authentication processing unit 360.

The authentication processing unit 360 according to the present embodiment performs an authentication process in order to determine whether or not there is an access right to the databases in the management device 300A.

More specifically, the authentication processing unit 360 provides result information stored in the result database 350 to a user whose user information is stored in the user information database 330.

For example, when the management device 300A receives a set of a user ID and a password from the terminal device 30, the management device 300A determines whether or not the set of the user ID and password are stored in the user information database 330 by using the authentication processing unit 360. When the authentication processing unit 360 determines that the corresponding set of the user ID and the password is found in the user information database, 330, the management device 300A extracts, from the result database 350, result information including the input user ID, and transmits the result information to the terminal device 30.

Further, for example, when an authentication code or the like that is pre-assigned to a medical institution or an eyewear shop provided with the eye examination device 10 is entered, the management device 300A according to the present embodiment may transmit the result information associated with the authentication code to the terminal device 30 from which the authentication code is entered. In this case, in the management device 300A, for each authentication code, user ID(s) included in the result information to be transmitted may be associated with the corresponding authentication code.

In the present embodiment, by grouping the result information for each authentication code, the result information of particular subject(s) can be provided, for example, to an educational institution such as a school for the blind, an association for persons with poor eyesight, or a support organization.

Fourth Embodiment

A fourth embodiment will be described below with reference to the drawings. The fourth embodiment describes application of the parameter information to an eyewear. In the description of the fourth embodiment below, an element having a functional configuration similar to that of the first to third embodiments will be given a symbol similar to that used in the description of the first to third embodiments, and the description thereof will be omitted.

Figure 21:
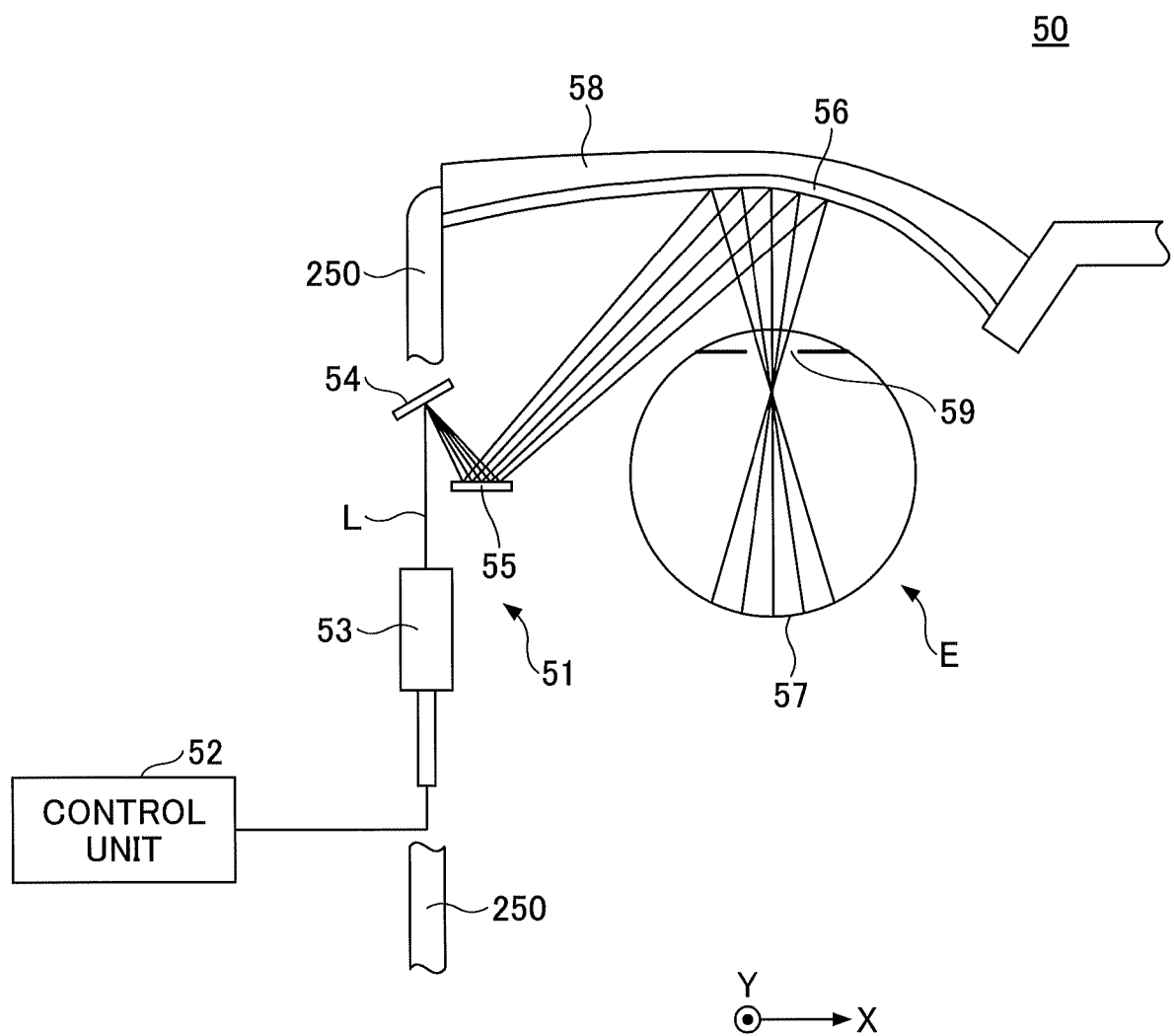
FIG. 21 is a diagram illustrating a structure of a retinal scanning type eyewear.

First, a structure of the eyewear 50 will be described with reference to FIG. 21. FIG. 21 is a diagram illustrating the structure of a retinal scanning type eyewear. FIG. 21 illustrates a top view of the eyewear 50.

The eyewear 50 according to the present embodiment includes a projection unit 51 and a control unit 52. The projection unit 51 according to the present embodiment includes a light source 53, a scanning mirror 54, a reflection mirror 55, and a projection mirror 56.

In the eyewear 50 of the present embodiment, let a direction in which a light beam having entered the projection mirror 56 travels be an X-direction, and let a direction perpendicular to the X-direction in the projection mirror 56 be a Y-direction.

The scanning mirror 54 is a MEMS mirror, for example. The scanning mirror 54 scans laser light (light beam) L emitted from light source 53 in two dimensions, horizontally and vertically. The scanning mirror 54 also scans the light beam L emitted from the light source 53 in two dimensions to provide a projection light for projecting an image onto a retina 57 of a user's eyeball E.

The reflection mirror 55 reflects the light beam L scanned by the scanning mirror 54 toward a lens 58.

The projection mirror 56 having a freeform surface is provided on a surface of the lens 58 at a side of the user's eyeball E. The projection mirror 56 projects an image to the retina 57 by irradiating the retina 57 of the eyeball E with the light beam L that has been scanned by the scanning mirror 54 and that has been reflected by the reflection mirror 55. That is, the user can recognize the image by an afterimage caused by the laser light projected onto the retina 57. The projection mirror 56 is designed such that a converging position of the light beam L scanned by the scanning mirror 54 is a pupil 59 of eyeball E. The light beam L enters the projection mirror 56 almost horizontally (i.e., almost from a —X direction).

In the present embodiment, if a curvature of the freeform surface of the projection mirror 56 is increased, a distance from the reflection mirror 55 to the converging position of the pupil 59 can be shortened, and the eyewear 50 can be reduced in size.

The control unit 52 of the present embodiment may be implemented, for example, by the terminal device 30 or the terminal device 30A.

Next, the application of the parameter information obtained by the eye examination using the eye examination device 10 to the eyewear 50 will be described. With reference to FIGS. 22A and 22B, a method of applying the pupil-to-pupil distance in the parameter information 119 to the eyewear 50 will be described.

FIG. 22A illustrates an eyewear prior to the application of the pupil-to-pupil distance, and FIG. 22B illustrates an eyewear after the application of the pupil-to-pupil distance.

In the eyewear 50 according to the present embodiment, a laser emitting unit 60 is provided on a left eye side. The light source 53, the scanning mirror 54, the reflection mirror 55, and the projection mirror 56 are included in this laser emitting unit 60.

The laser emitting unit 60 is mounted to a frame of the eyewear 50 in a manner movable in the X-direction and the Y-direction, and the pupil-to-pupil distance of the parameter information 119 is reflected in the X-direction of the laser emitting unit 60.

In the present embodiment, for example, as illustrated in FIG. 22B, by moving the laser emitting unit 60 in the X-direction in accordance with a value of a pupil-to-pupil distance, the position of the laser emitting unit 60 adapted to the pupil-to-pupil distance of each user can be determined.

In order to move the laser emitting unit 60 in the X-direction, by inserting a spacer Sa or the like having a thickness corresponding to the pupil-to-pupil distance between a temple 49 and the laser emitting unit 60, the position of the laser emitting unit 60 can be adjusted in accordance with the pupil-to-pupil distance, without using a complicated mechanism. Note that a configuration of moving the laser emitting unit 60 is not limited thereto, and other configurations, such as a configuration of moving the laser emitting unit 60 along the guide groove, may be adopted.

Although the present invention has been described based on the embodiments, the present invention is not limited to the requirements described herein, such as the configurations described above and combinations with other elements. These configurations can be changed to the extent that the gist of the present invention is not impaired, and can be suitably defined in accordance with application forms.

This international application is based on and claims priority to Japanese Patent Application No. 2016-253984 filed on Dec. 27, 2016, the entire contents of which are incorporated herein by reference.

DESCRIPTION OF REFERENCE SYMBOLS 10 eye examination device
16 eyepiece device
30, 30A terminal device
31 deflection angle setting processing unit
40 parameter information
50 eyewear
60 laser emitting unit
100, 100A, 100B eyewear provision system
110 eye examination processing unit
200 eye examination system
300, 300A management device
310 eye examination management processing unit
330 user information database
340 attribute mapping database
350 result database
360 authentication processing unit

What is claimed is:

1. A retinal scanning type eye examination device comprising:
a storage unit configured to store test image data;
a laser emitting unit including a laser light source configured to generate an imaging laser beam based on the test image data, the laser emitting unit being configured to project, by using the imaging laser beam, a test image on a retina of an eyeball of a person subjected to an eye examination;
an optical component configured to cause the imaging laser beam to converge at an inside of the eyeball of the person;
a parameter acquiring unit configured to acquire parameter information for a retinal scanning type eyewear, the parameter information including angle information indicating a rotation angle of the laser emitting unit when the laser emitting unit is rotated around a converging point of the laser beam; and
an output unit configured to output the parameter information to an external device.

2. The retinal scanning type eye examination device according to claim 1, further comprising:
an operation receiving unit configured to receive an operation by the person; and
a mechanism controller configured to perform a position control of the laser emitting unit in accordance with the operation, the position control including at least one of translation and rotation;
wherein the angle information indicates the rotation angle of the laser emitting unit when the laser emitting unit is rotated by the mechanism controller, and
the parameter information includes position information indicating a position of the laser emitting unit when the laser emitting unit is translated by the mechanism controller, the position information including information indicating a pupil-to-pupil distance of the person.

3. The retinal scanning type eye examination device according to claim 1, further comprising an input unit configured to receive an input of a result of visually recognizing the test image by the person; wherein the output unit is configured to output eye examination result information indicating the result of visually recognizing the test image by the person.

4. The retinal scanning type eye examination device according to claim 1, further comprising a scanning unit configured to scan the imaging laser beam; wherein
the parameter information includes optical scanning angle information of the scanning unit.

5. A retinal scanning type eye examination system comprising:
a retinal scanning type eye examination device that performs an eye examination of a person, and a management device connected to the retinal scanning type eye examination device; wherein
the retinal scanning type eye examination device includes
a storage unit configured to store test image data,
a laser emitting unit including a laser light source configured to generate an imaging laser beam based on the test image data, the laser emitting unit being configured to project, by using the imaging laser beam, a test image on a retina of an eyeball of the person,
an optical component configured to cause the imaging laser beam to converge at an inside of the eyeball of the person,
a parameter acquiring unit configured to acquire parameter information for a retinal scanning type eyewear, the parameter information including angle information indicating a rotation angle of the laser emitting unit when the laser emitting unit is rotated around a converging point of the laser beam, and
an output unit configured to output the parameter information to the management device; and
the management device includes a parameter transmitting unit configured to transmit the parameter information to a terminal device.

6. The retinal scanning type eye examination system according to claim 5, the retinal scanning type eye examination device further including
an operation receiving unit configured to receive an operation by the person; and
a mechanism controller configured to perform a position control of the laser emitting unit in accordance with the operation, the position control including at least one of translation and rotation;
wherein the angle information indicates the rotation angle of the laser emitting unit when the laser emitting unit is rotated by the mechanism controller, and
the parameter information includes position information indicating a position of the laser emitting unit when the laser emitting unit is translated by the mechanism controller, the position information including information indicating a pupil-to-pupil distance of the person.

7. The retinal scanning type eye examination system according to claim 6, wherein
the retinal scanning type eye examination device includes an input unit configured to receive an input of a result of visually recognizing the test image by the person,
the output unit is configured to output, to the management device, eye examination result information indicating the result of visually recognizing the test image by the person, and
the management device includes
an eyeball condition detecting unit configured to output eyeball condition information indicating a condition of the eyeball of the person based on the eye examination result information, and
a result storing unit configured to store, into a storage region, result information having the parameter information, the eye examination result information, and the eyeball condition information associated with each other.

8. The retinal scanning type eye examination system according to claim 5, the retinal scanning type eye examination device including a scanning unit configured to scan the imaging laser beam; wherein the parameter information includes optical scanning angle information of the scanning unit.

9. An eyewear provision system comprising:
a retinal scanning type eye examination device that performs an eye examination of a person, and a terminal device configured to perform communication with the retinal scanning type eye examination device;
the retinal scanning type eye examination device including
a storage unit configured to store test image data,
a laser emitting unit including a laser light source configured to generate an imaging laser beam based on the test image data, the laser emitting unit being configured to project, by using the imaging laser beam, a test image on a retina of an eyeball of the person,
an optical component configured to cause the imaging laser beam to converge at an inside of the eyeball of the person,
a parameter acquiring unit configured to acquire parameter information for a retinal scanning type eyewear, the parameter information including angle information indicating a rotation angle of the laser emitting unit when the laser emitting unit is rotated around a converging point of the laser beam, and
an output unit configured to output the parameter information to the terminal device.

10. The eyewear provision system according to claim 9, the retinal scanning type eye examination device further including
an operation receiving unit configured to receive an operation by the person; and
a mechanism controller configured to perform a position control of the laser emitting unit in accordance with the operation, the position control including at least one of translation and rotation;
wherein the angle information indicates the rotation angle of the laser emitting unit when the laser emitting unit is rotated by the mechanism controller, and
the parameter information includes position information indicating a position of the laser emitting unit when the laser emitting unit is translated by the mechanism controller, the position information including information indicating a pupil-to-pupil distance of the person.

11. The eyewear provision system according to claim 9, wherein the terminal device is able to be connected with a manufacturing apparatus of a retinal scanning type head-mounted display.

12. A retinal scanning type eyewear comprising:
a light source configured to generate a light beam;
an image input unit configured to input image data;
a control unit configured to generate an imaging light beam based on the input image data, and to control emission of the imaging light beam from the light source;
a scanning mirror configured to scan the imaging light beam; and
a projection unit configured to project, as an image represented by the image data, the imaging light beam onto a retina of an eyeball of a user; wherein a position of the light source is determined based on parameter information for the retinal scanning type eyewear, the parameter information being obtained by an external retinal scanning type eye examination device including a laser emitting unit configured to emit a laser light beam, and the parameter information includes angle information indicating a rotation angle of the laser emitting unit when the laser emitting unit is rotated around a converging point of the laser beam in the retinal scanning type eye examination device, the converging point being obtained by the retinal scanning type eye examination device by projecting a test image onto the retina of the eyeball of the user and by causing the laser beam to converge at an inside of the eyeball of the user.

13. The retinal scanning type eyewear according to claim 12, the retinal scanning type eye examination device further comprising an operation receiving unit configured to receive an operation by the person; and a mechanism controller configured to perform a position control of the laser emitting unit in accordance with the operation, the position control including at least one of translation and rotation;

wherein the angle information indicates the rotation angle of the laser emitting unit when the laser emitting unit is rotated by the mechanism controller, and the parameter information includes position information indicating a position of the laser emitting unit when the laser emitting unit is translated by the mechanism controller, the position information including information indicating a pupil-to-pupil distance of the user.

* * * * *